(12) United States Patent
Ternes et al.

(10) Patent No.: US 9,026,214 B2
(45) Date of Patent: May 5, 2015

(54) SYSTEMS AND METHODS FOR AVOIDING ASPIRATION DURING AUTONOMIC MODULATION THERAPY

(75) Inventors: David J. Ternes, Roseville, MN (US); Shantha Arcot-Krishnamurthy, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/495,283

(22) Filed: Jun. 13, 2012

(65) Prior Publication Data
US 2012/0330373 A1   Dec. 27, 2012

Related U.S. Application Data

(60) Provisional application No. 61/500,293, filed on Jun. 23, 2011.

(51) Int. Cl.
*A61N 1/18* (2006.01)
*A61N 1/36* (2006.01)

(52) U.S. Cl.
CPC ......... *A61N 1/36053* (2013.01); *A61N 1/36135* (2013.01); *A61N 1/36142* (2013.01)

(58) Field of Classification Search
USPC ........ 607/2, 7, 9, 27, 28, 42, 62, 66; 600/529, 600/532, 533, 538, 539, 586
See application file for complete search history.

(56) References Cited

U.S. PATENT DOCUMENTS

| | | | |
|---|---|---|---|
| 5,205,285 A | 4/1993 | Baker | |
| 6,097,984 A * | 8/2000 | Douglas | 607/40 |
| 7,142,817 B2 | 11/2006 | Hankui | |
| 7,336,997 B2 | 2/2008 | Fukui | |
| 7,551,958 B2 | 6/2009 | Libbus et al. | |
| 7,606,623 B2 | 10/2009 | Ludlow et al. | |
| 7,672,728 B2 | 3/2010 | Libbus et al. | |
| 7,925,342 B2 * | 4/2011 | Amurthur et al. | 607/2 |
| 8,148,394 B2 | 4/2012 | Edwards et al. | |
| 2008/0051839 A1 | 2/2008 | Libbus et al. | |
| 2008/0058872 A1 * | 3/2008 | Brockway et al. | 607/2 |
| 2008/0058874 A1 * | 3/2008 | Westlund et al. | 607/2 |
| 2008/0234780 A1 | 9/2008 | Smith et al. | |
| 2009/0012433 A1 | 1/2009 | Fernstrom et al. | |
| 2009/0228079 A1 | 9/2009 | Libbus | |
| 2010/0076279 A1 | 3/2010 | Shuros et al. | |
| 2011/0015704 A1 | 1/2011 | Ternes et al. | |
| 2011/0125212 A1 * | 5/2011 | Tyler | 607/42 |

OTHER PUBLICATIONS

Arcot-Krishnamurthy, Shantha, et al., "Systems and methods for using electrical impedance for neuro cardiac therapy", U.S. Appl. No. 13/309,320, filed Dec. 1, 2011.
Arcot-Krishnamurthy, Shantha, et al., "Systems and Methods for Using Sensed Pressure for Neuro Cardiac Therapy", U.S. Appl. No. 13/309,328, filed Dec. 1, 2011.

* cited by examiner

*Primary Examiner* — Rex R Holmes
(74) *Attorney, Agent, or Firm* — Schwegman Lundberg & Woessner, P.A.

(57) ABSTRACT

Some embodiments provide a method comprising delivering neural stimulation for a neural stimulation therapy according to a programmed schedule, detecting a swallow event, and responding to the detected swallow event by overriding the programmed schedule.

22 Claims, 16 Drawing Sheets

SYSTEMS AND METHODS FOR AVOIDING ASPIRATION DURING AUTONOMIC MODULATION THERAPY

CLAIM OF PRIORITY

This application claims the benefit of priority under 35 U.S.C. §119(e) of Temes et al., U.S. Provisional Patent Application Ser. No. 61/500,293, entitled "SYSTEMS AND METHODS FOR AVOIDING ASPIRATION DURING AUTONOMIC MODULATION THERAPY", filed on Jun. 23, 2011, which is herein incorporated by reference in its entirety.

TECHNICAL FIELD

This application relates generally to medical devices and, more particularly, to systems, devices and methods for delivering neural stimulation.

BACKGROUND

Neural stimulation, such as vagus nerve stimulation, has been proposed as a therapy for a number of conditions. Examples of neural stimulation therapies include neural stimulation therapies for respiratory problems such as sleep disordered breathing, blood pressure control such as to treat hypertension, cardiac rhythm management, myocardial infarction and ischemia, heart failure (HF), epilepsy, depression, pain, migraines, eating disorders and obesity, and movement disorders.

SUMMARY

Some embodiments provide a method comprising delivering neural stimulation for a neural stimulation therapy according to a programmed schedule, detecting a swallow event, and responding to the detected swallow event by overriding the programmed schedule.

Some embodiments provide a method comprising delivering neural stimulation for a neural stimulation therapy according to a programmed schedule, detecting dysphagia, and enabling a swallow override routine in response to detecting dysphagia. The swallow override routine includes detecting a swallow event, and responding to the detected swallow event by overriding the programmed schedule.

Some embodiments provide a method comprising delivering neural stimulation for a neural stimulation therapy according to a programmed schedule, detecting a laryngeal spasm, and responding to the detected laryngeal spasm by temporarily overriding the programmed schedule for a programmed time period.

Some embodiments provide a method comprising delivering neural stimulation for a neural stimulation therapy according to a programmed schedule, detecting pharyngitis, and responding to the detected pharyngitis by temporarily overriding the programmed schedule for a programmed time period.

Some embodiments provide a method comprising delivering neural stimulation for a neural stimulation therapy according to a programmed schedule, detecting inflammation that satisfies a threshold, and responding to the detected inflammation by temporarily overriding the programmed schedule for a programmed time period.

Some embodiments provide a method comprising delivering neural stimulation for a neural stimulation therapy according to a programmed schedule, monitoring breathing and detecting a change in breathing that satisfies a threshold, and responding to the detected change by temporarily overriding the programmed schedule for a programmed time period.

Some embodiments provide an implantable device, comprising a neural stimulation circuit configured to deliver neural stimulation according to a programmed schedule, and an event detector configured to detect at least one event, wherein the event detector is configured to detect a swallow event, a laryngeal spasm event, a pharyngitis event, an asthma event, or a dysphagia event. The neural stimulation circuit includes a therapy override controller configured to respond to a detected event, detected by the event detector, and override the programmed schedule for delivering neural stimulation.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
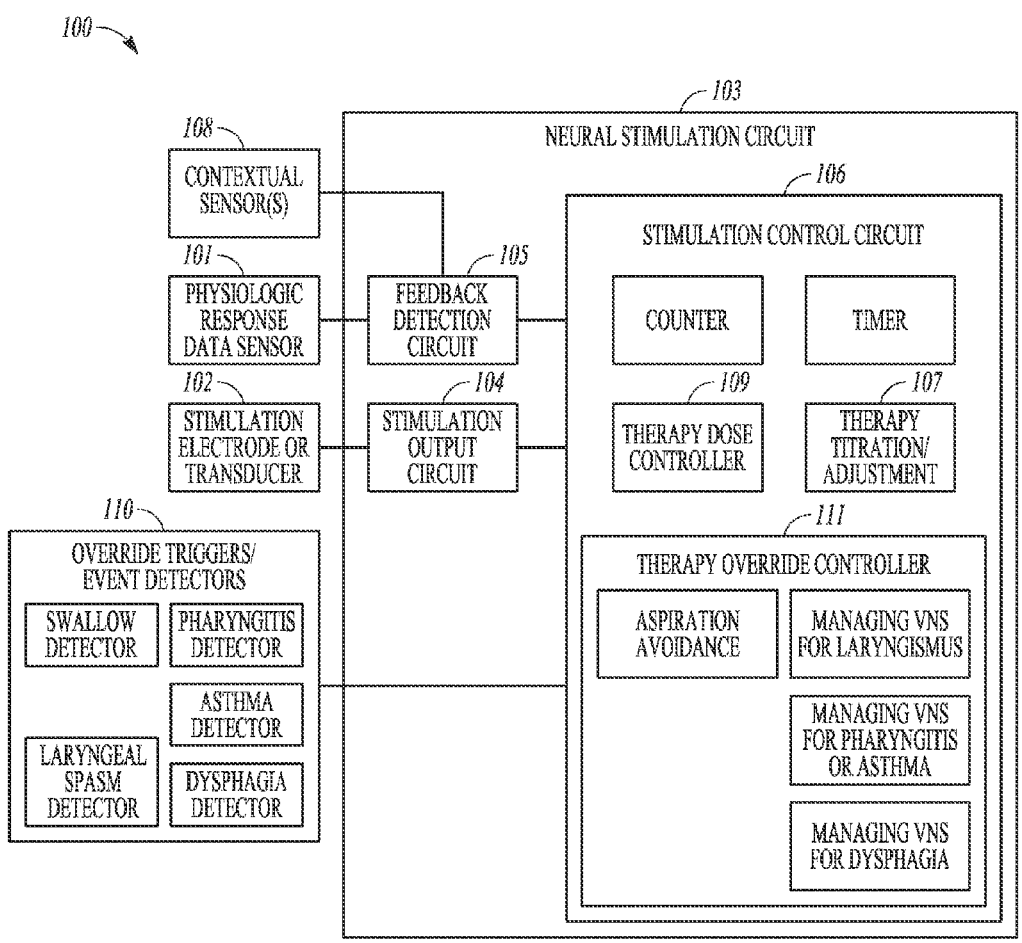
FIG. 1 is a block diagram illustrating an embodiment of a circuit of a neural stimulation system.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The autonomic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscles around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system. Afferent nerves convey impulses toward a nerve center, and efferent nerves convey impulses away from a nerve center.

Stimulating the sympathetic and parasympathetic nervous systems can cause heart rate, blood pressure and other physiological responses. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intestine, increases urine secretion, and contracts the wall and relaxes the sphincter of the bladder. The functions associated with the sympathetic and parasympathetic nervous systems are many and can be complexly integrated with each other.

A reduction in parasympathetic nerve activity contributes to the development and progression of a variety of cardiovascular diseases. Some embodiments of the present subject matter can be used to prophylactically or therapeutically treat various cardiovascular diseases using autonomic modulation therapy (AMT) to stimulate nerves and thereby modulate autonomic tone. Neural stimulation to treat cardiovascular diseases is referred to herein as neurocardiac therapy (NCT). Vagal stimulation used to treat cardiovascular diseases may be termed either vagal stimulation therapy (VST) or NCT. However, VST may be delivered for non-cardiovascular diseases, and NCT may be delivered by stimulating a nerve other than the vagal nerve. Both VST and NCT are examples of AMT. Examples of cardiovascular diseases or conditions include hypertension, HF, and cardiac remodeling. These conditions are briefly described below.

Hypertension is a cause of heart disease and other related cardiac comorbidities. Hypertension occurs when blood vessels constrict. As a result, the heart works harder to maintain flow at a higher blood pressure, which can contribute to HF. Hypertension generally relates to high blood pressure, such as a transitory or sustained elevation of systemic arterial blood pressure to a level that is likely to induce cardiovascular damage or other adverse consequences. Hypertension has been defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease. A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

HF refers to a clinical syndrome in which cardiac function causes a below normal cardiac output that can fall below a level adequate to meet the metabolic demand of peripheral tissues. HF may present itself as congestive heart failure (CHF) due to the accompanying venous and pulmonary congestion. RE can be due to a variety of etiologies such as ischemic heart disease. HF patients have impaired autonomic balance, which is associated with LV dysfunction and increased mortality.

Cardiac remodeling refers to a complex remodeling process of the ventricles that involves structural, biochemical, neurohormonal, and electrophysiologic factors, which can result following a myocardial infarction (MI) or other cause of decreased cardiac output. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation. As the heart begins to dilate, afferent baroreceptor and cardiopulmonary receptor signals are sent to the vasomotor central nervous system control center, which responds with hormonal secretion and sympathetic discharge. The combination of hemodynamic, sympathetic nervous system and hormonal alterations (such as presence or absence of angiotensin converting enzyme (ACE) activity) account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

Vagus nerve stimulation therapy for heart failure, hypertension, and other conditions may stimulate the vagus nerve within the carotid sheath in the cervical region of the patient. Four major structures contained within the carotid sheath are the vagus nerve, the internal jugular vein, the common carotid artery, and the deep cervical lymph nodes. The carotid artery lies medial to the internal jugular vein and the vagus nerve is situated posterior between the two vessels. In the upper part, the carotid sheath also contains the glossopharyngeal nerve (IX), the accessory nerve (XI), and the hypoglossal nerve (XII), all which pierce the fascia of the carotid sheath. The ansa cervicalis is embedded in the anterior wail of the sheath. It is formed by the "descendens hypoglossi" (C1) and "descendens cervicalis" (C2-C3). Placement of the lead caudal to the ansa might prevent capture of the ansa, and hence capture of muscles innervated by the ansa.

Vagal nerve stimulation may cause some undesirable or adverse events, such as voice alteration, increased cough, dyspnea (abnormal breathing or uncomfortable feeling of breathlessness or shortness of breath), dysphagia (difficulty swallowing), laryngismus (uncontrolled, involuntary spasms of the laryngeal cords), pharyngitus (inflammation of the pharynx).

Voice alteration occurs when the vagus nerve stimulation also captures the recurrent laryngeal nerve causing hoarseness or a modulation of the voice at the stimulation frequency. Not all patients exhibit voice alteration, even if the delivered stimulation to a cervical vagus nerve causes laryngeal vibrations.

Furthermore, stimulation of the left vagus nerve appears to directly stimulate the left laryngeal recurrent nerve without hardly any response for the right vocal cord indicating that there is little contra-lateral innervations of the laryngeal muscles and indicating that the left laryngeal recurrent nerve is not stimulated through reflexes via the brainstem but rather is directly stimulated (see "Vagus nerve stimulation for epilepsy activates the vocal folds maximally at therapeutic levels" by J. J. Ardesch, et al., (Epilepsy Research (2010))). Thus, for example, if the right cervical vagus nerve is stimulated, the right laryngeal recurrent nerve is affected with little response for the left vocal cord.

A hypothesis concerning dyspnea invoked by vagal nerve stimulation is that vagal nerve stimulation evokes reflexes that modulate pulmonary airways and possibly the laryngeal airway resistance, and that these evoked reflexes may result dyspnea or apnea. Another hypothesis is that the stimulation of the laryngeal muscles alters breathing patterns, either consciously or unconsciously, and that the uneven innervations of the laryngeal muscles (left vs. right) affects breathing patterns and laryngeal airway resistance.

A hypothesis concerning dysphagia, laryngismus, pharyngitus and/or increased cough invoked by vagal nerve stimulation is that vagal nerve stimulation alters the mechanics of swallowing. The altered mechanics of swallowing may lead to dysphagia, the altered mechanics of swallowing may lead to aspiration, and the dysphagia itself may lead to aspiration. Aspiration can directly cause laryngismus. Laryngismus may also possibly be caused by the stimulation of the recurrent laryngeal nerve irritating the larynx and larynx muscles. This irritation may be further exacerbated by the uneven or lopsided innervations of the laryngeal muscles (left vs. right). In support of this hypothesis, it is noted that aspiration is common in stroke victims (estimated 20% rate of death due to aspiration pneumonia in the first year after a stroke) and stroke typically affects only one side of the body.

Additionally, aspiration can lead to increased coughing to clear the airway and lungs. Although the cough reflex can be evoked if the vagal nerve stimulation is too high, one would assume that an attending physician would set the stimulation level below that which caused consistent coughing. Cough thresholds may be position or activity dependent. However, the physician would eventually change the stimulation parameters to avoid the cough reflex in the ambulatory patient, or the patient would alter their activity to avoid coughing. Additionally, it is known that the human body accommodates to VST, realizing a reduction of side effects to the VST over time. Therefore, the reported ambulatory increase in coughing appears to be caused by aspiration or "tickling" of the larynx. Irritation of the laryngeal muscles can lead to a "tickling" feeling and an increase in cough. The patient may learn consciously or unconsciously to avoid swallowing during VNS which leads to reductions in reported dysphagia and coughing.

Pharyngitus may be a direct result of constant coughing, irritation from "tickled" larynx muscles, or irritation from lopsided innervations. Pharyngitus has been reported as a side effect of vagal nerve stimulation even though vagal nerve stimulation has been reported to be anti-inflammatory, which normally would act to reduce inflammation of the pharynx.

Various embodiments provide systems, devices and methods for avoiding aspiration during AMT. Heart failure and hypertension patients, for example, are already at risk of aspiration pneumonia. Embodiments attempt to reduce the risk of aspiration when AMT is delivered for heart failure and hypertension, or other conditions.

When food is swallowed, the tongue pushes the food to the hack of the throat. Muscle contractions quickly move the food through the pharynx into the esophagus to the stomach. Normal swallowing involves coordination of the hyoid movement and laryngeal elevation to protect the airway and prevent aspiration during swallowing. The oropharyngeal stage of swallowing involves a reflex inhibition of respiratory movements and the coordinated, muscular contractions of the tongue, pharynx and larynx. As the food passes through the pharynx, the walls of the pharynx are relaxed and constricted, the epiglottis bends backward, and the larynx and trachea move upward and forward. The elevation of the soft palate prevents the food from entering the nasal cavity and the closure of the glottis and the epiglottis prevent the food from entering the larynx.

Stimulation of the recurrent laryngeal nerve, a branch of the vagus nerve, may impact the ability to properly coordinate and maintain the upward and forward movement of the larynx during the oropharyngeal stage. Because of this lack of coordination, the larynx may not completely close during the entire period of swallowing which can lead to aspiration, along with dysphagia, laryngismus and increased cough. Also, the lopsided stimulation of the laryngeal muscles (left vs. right) may result in uneven closure of the glottis or inclination of the epiglottis which may lead or further exacerbate improper closure of the larynx during swallowing.

The mechanics of swallowing may be compromised by the ansa cervicalis, a loop of nerves that lie superficial to the internal jugular vein in the carotid sheath. The vagus nerve and carotid artery also lie within the carotid sheath. Branches from the ansa cervicalis innervate three of the four infrahyoid muscles (the sternohyoid, sternothyroid, and the omohyoid muscles). The infrahyoid muscles, also known as the "strap" muscles, function to depress the hyoid bone and larynx during swallowing and speaking. The ansa cervicalis may be severed when the surgeon opens the carotid sheath to implant the cuff electrodes. Therefore, the implantation of the cuff electrodes on the cervical vagus nerve may compromise the mechanics of swallowing. The vagus nerve stimulation, whether the stimulation is delivered by nerve cuff or transvacularly using intravascular electrodes, may also capture part of the ansa cervicalis. If the vagus nerve stimulation captures part of the ansa cervicalis, the function of one or more of the infrahyoid muscles may be comprised, which may result in dysphagia, laryngismus, aspiration and/or increased coughing.

The mechanics of swallowing may be compromised by innervations of the levator yeti palatini, the elevator muscle of the soft palate. The levator yeti palatini contracts during swallowing to elevate the soft palate to help prevent food and liquid from entering the nasopharynx. The levator veli palatini is innervated via the pharyngeal plexus, primarily by the pharyngeal branch of the vagus nerve. Currently, it is not known if vagus nerve stimulation can cause side effects related to the innervations of the levator veli palatini. However, it may be possible that unintended capture or injury to the levator veli palatini may result dysphagia or pharyngitis. For example, some stimulation delivery systems place electrodes in the carotid sheath to target stimulation of the vagus nerve or another neural target such as the carotid sinus nerve, and some stimulation delivery systems place electrodes inside the internal jugular vein or other vessel for a neural target. As the electrodes are not wrapped around the target nerve, there may be greater potential of electrically stimulating structures other than the target nerve.

Various embodiments detect swallow events and use detected swallow events to manage vagus nerve stimulation. Generally, it is not required to identify every swallow event for the purpose of managing vagus nerve stimulation around swallows nor is it a major issue to falsely identify a swallow event as occurring. However, it is desirable to accurately detect swallow events and avoid false positives to aid in the reduction of side effects such as dysphagia or increased cough while maintaining the efficacy of the vagus nerve stimulation.

Swallowing may be detected using implantable sensing technology, such as technology that uses electromyographs (EMG), pressure sensors, or sounds detected via an accelerometer or microphone. Swallowing can be distinguished from breathing, coughing, speaking, rales or other sounds generated in or near the neck region.

Swallowing, breathing, and speaking are distinguishable from one another using external microphones or accelerometers or using internally implanted EMG, pressure, XL and/or sound sensors. There are distinct patterns among normal breathing, rates, and sonorous rhonchus sounds, and there are distinct patterns between normal breathing and asthmatic breathing. Such distinct patterns allow for approaches to identify and discriminate between various sound patterns. Also, there are distinguishable characteristics between various lung sounds such as different crackles and different wheezes.

FIG. 1 is a block diagram illustrating an embodiment of a circuit of a neural stimulation system 100. The system 100 includes a data sensor 101 adapted to sense a physiologic response to the neural stimulation, a stimulation electrode/transducer 102, and a neural stimulation circuit 103. The neural stimulation circuit 103 includes a stimulation output circuit 104, a feedback detection circuit 105, and a stimulation control circuit 106. The stimulation control circuit 106 controls the delivery of the neural stimulation pulses and includes a therapy titration adjustment circuit or module 107. The stimulation output circuit 104 delivers the neural stimulation pulses upon receiving a pulse delivery signal or signals from stimulation control circuit 106. The data sensor 101 provides signals indicative of a physiological response to the applied neural stimulation. The feedback detection circuit 105 receives the signal(s) indicative of the response and processes the signal(s) to provide a neural stimulation feedback signal. Some embodiments provide open loop neural stimulation therapy, and thus do no include the feedback detection circuit 105 or physiologic response data sensor 101 or contextual sensor(s) 108). In various embodiments, the response includes a cardiac activity such as heart rate, HRV, HRT, PR interval, T-wave velocity, or action potential duration. In various embodiments the response includes a non-cardiac response such as respiration or blood pressure. In various embodiments, the response includes a QT interval or atrial/ventricular refractory periods. In some embodiments, the therapy titration/adjustment module 107 uses the feedback signal to modulate or titrate the therapy generated by the stimulation output circuit 104 to provide the desired physiologic response (e.g. cardiac response or non-cardiac response). Some embodiments include contextual sensor(s) or input(s) 108 connected to the feedback detection circuit 105 to provide a more complete picture of a patient's physiology. The feedback detection circuit can provide the neural stimulation feedback signal based on the physiological response data sensor(s) 101 and the contextual input(s) 108. The contextual input(s) can be used to avoid incomplete data from affecting the neural stimulation. Examples of contextual inputs include an activity sensor, a posture sensor and a timer. Another example of a contextual input is an input that is indicative of a patient's environment (e.g. in bedroom or car). Any one or combination of two or more contextual inputs can be used by the feedback detection circuit. For example, an elevated heart rate may be representative of exercise rather than a reason for titrating the neural stimulation therapy. The illustrated stimulation control circuit 106 includes a therapy dose controller 109, which is configured to determine a desired neural stimulation therapy dose for the patient. The therapy dose controller 109 is configured to control the stimulation parameters (e.g. amplitude, pulse width, pulse frequency, burst duration, etc.). Some embodiments use a counter or timer to provide the desired dose. In some embodiments, the illustrated therapy dose controller 109 includes a therapy monitor and a timer, and is configured to determine an amount of the therapy over a defined therapy window, compare the amount of the therapy over the defined therapy window to a defined therapy amount, and make appropriate adjustments if the amount of the therapy over the defined therapy window is different than the defined therapy amount. The therapy dose controller 109, feedback detection circuit 105 and therapy titration/adjustment circuit 107 are configured to cooperate to provide the desired therapy dose for the patient.

The system 100 includes event detector(s) 110 that function as override triggers that trigger an override of the neural stimulation therapy. According to various embodiments, the illustrated system includes a swallow detector, or a laryngeal spasm detector, or a pharyngitis detector, or an asthma detector, or, a dysphagia detector, or any combination of two or more of the swallow detector, the laryngeal spasm detector, the pharyngitis detector, the asthma detector, or the dysphagia detector. Examples of swallow detectors include EMG sensors, pressure sensors, and sound detectors from an accelerometer or microphone. Examples of laryngeal spasm detectors include EMG sensors, accelerometer sensors, and minute ventilation sensors that can be used to detect difficult breathing. A laryngeal spasm can be characterized by the duration of the muscle contraction activity. The spasms can last from several seconds to over a minute and become more uncomfortable the longer the duration. Examples of pharyngitis detectors include temperature sensors which may be used to detect an accompanying fever, and impedance sensors which may be used monitor impedance changes across the pharynx to detect swollen glands. Pharyngitis may also be detected by monitoring swallow patterns in addition to the monitoring for inflammation. Swallow patterns may change with a swollen sore pharynx because of discomfort. A single swallow may lengthen in duration, or the timing between muscle group activation may change as the individual attempts to control the pain associated with pharyngitis. In addition, the discomfort associated with pharyngitis may result in fewer swallows or a group of rapid swallows followed by a cessation of swallowing for a period of time as the individual attempts to control the pain associated with pharyngitis. The pharyngitis sensor may be a blend of the impedance monitor for inflammation with the swallow morphology or swallow pattern monitor. A dysphagia detector, for example, may monitor for changes in swallowing. Swallow morphology may be monitored. Swallow patterns may be monitored. Some embodiments monitor for several aborted attempts to swallow or a pattern related to gagging. Some embodiments monitor for fewer swallows or groups of swallows. A swallow detector may be used to monitor for a decrease in frequency of swallows.

The illustrated stimulation control circuit 106 also includes a therapy override controller 111 configured to provide a response to the event(s) detected by the event detector 110. The illustrated therapy override controller 111 includes processes or programmed algorithms for responding to override triggers or event detectors, for avoiding aspiration, for responding to laryngismus, or for responding to asthma, or for responding to dysphagia. In various embodiments, the therapy override controller 111 includes processes or algorithms for responding to any combination of two or more of avoiding aspiration, responding to laryngismus, responding to pharyngitis, responding to asthma, or responding to dysphagia.

Figure 2:
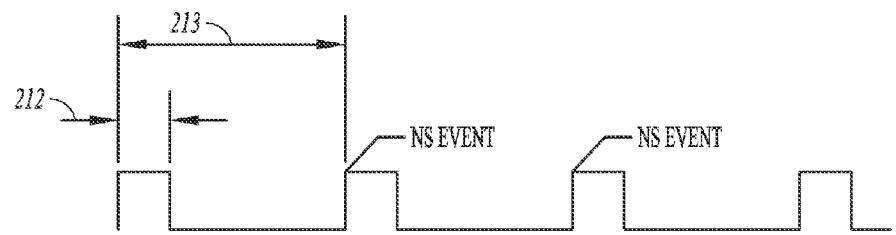
FIG. 2 illustrates a representation of intermittent neural stimulation (INS).

In some embodiments, the neural stimulation is delivered as part of a chronic neural stimulation therapy for a chronic disease such as heart failure or hypertension. Such chronic neural stimulation can be delivered using intermittent neural stimulation. FIG. 2 illustrates a representation of intermittent neural stimulation (INS). The figure diagrammatically shows the time-course of a neural stimulation that alternates between intervals of stimulation being ON, when one stimulation pulse or a set of grouped stimulation pulses (i.e., a burst 212) is delivered, and intervals of stimulation being OFF, when no stimulation pulses are delivered. Thus, for example, some embodiments deliver a plurality of monophasic or biphasic pulses within a neural stimulation burst illustrated in FIG. 2. Pulses delivered within a burst 212 may be delivered at a pulse frequency. These pulses also have an amplitude. The pulse frequency, the pulse amplitude and the pulse width affect the dose of the neural stimulation therapy. The duration of the stimulation ON interval is sometimes referred to as the stimulation duration or burst duration. The burst duration also affects the dose of the neural stimulation therapy. The start of a stimulation ON interval is a temporal reference point NS Event. The time interval between successive NS Events is the INS interval, which is sometimes referred to as the stimulation period or burst period 213. The burst period 213 or the number of neural stimulation events that occur over a time period also affect the dose of the neural stimulation. For an application of neural stimulation to be intermittent, the stimulation duration (i.e., ON interval) is less than the stimulation period (i.e., INS Interval) when the neural stimulation is being applied. The duration of the OFF intervals of INS are determined by the durations of the ON interval and the INS Interval. The duration of the ON interval relative to the INS Interval (e.g., expressed as a ratio) is sometimes referred to as the duty cycle of the INS.

Titration, as used herein, refers to the process of adjusting the dose of the stimulation, ultimately to a level that is therapeutically or prophylactically effective. The titration procedure may occur during an implantation procedure, or during a follow-up clinical visit, or while a patient is ambulatory away from the clinical setting. The titration may be physician-controlled or automatically-controlled based on device programming. As described in this document, some embodiments adjust the adjustable stimulation parameters used to titrate the therapy to temporarily reduce the stimulation intensity in response to a detected override event, and then subsequently increase the stimulation intensity to continue to deliver the desired dose of the neural stimulation. The dose includes an amount or intensity of the neural stimulation at a given time frame, and also includes the number of times the neural stimulation is delivered over a period of time. The intensity of the neural stimulation may be adjusted by adjusting parameters such as amplitude, duty cycle, duration, and or frequency of the neural stimulation, or the number of neural stimulation events that occur over a period of time.

Figure 3:
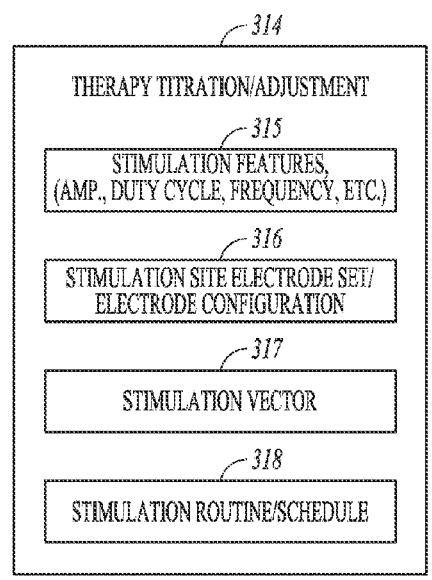
FIG. 3 illustrates an embodiment of a therapy adjustment module.

FIG. 3 illustrates an embodiment of a therapy titration module 314, which may also be referred to as a therapy adjustment module. According to various embodiments, the stimulation control circuit is adapted to set or adjust any one or any combination of stimulation features 315. Examples of stimulation features include the amplitude, pulse width, frequency, polarity and wave morphology of the stimulation signal. Examples of wave morphology include a square wave, triangle wave, sinusoidal wave, and waves with desired harmonic components to mimic naturally-occurring baroreflex stimulation. Some embodiments of the stimulation output circuit are adapted to generate a stimulation signal with a predetermined amplitude, morphology, pulse width and polarity, and are further adapted to respond to a control signal from the controller to modify at least one of the amplitude, wave morphology, pulse width and polarity. Some embodiments of the neural stimulation circuitry are adapted to generate a stimulation signal with a predetermined frequency, and are further adapted to respond to a control signal from the controller to modify the frequency of the stimulation signal.

The therapy titration module 314, also referred to as a therapy adjustment module, can be programmed to change an electrode set or electrode configuration or to change stimulation sites 316, such as changing the stimulation electrodes used for a neural target or changing the neural targets for the neural stimulation. For example, different electrodes can be used to stimulate a neural target, and different electrodes can be used to stimulate different neural targets. A desirably low stimulation threshold for a neural target may be determined using different electrode sets/configurations for stimulating that neural target. Different neural targets can include different neural pathways such as the right and left vagus nerves and branches thereof, baroreceptors, the carotid sinus, and the carotid sinus nerve. Different neural targets may include different positions along a neural pathway (e.g. more caudal or more cranial targets along a cervical vagus nerve). Autonomic neural targets can include afferent pathways and efferent pathways and can include sympathetic and parasympathetic nerves. The stimulation can include stimulation to stimulate neural traffic or stimulation to inhibit neural traffic. Thus, stimulation to evoke a sympathetic response can involve sympathetic stimulation and/or parasympathetic inhibition; and stimulation to evoke a parasympathetic response can involve parasympathetic stimulation and/or sympathetic inhibition.

The therapy titration module 314 can be programmed to change stimulation vectors 317. Vectors can include stimulation vectors between electrodes, or stimulation vectors for transducers. For example, the stimulation vector between two electrodes can be reversed. More complicated combinations of electrodes can be used to provide more potential stimulation vectors between or among electrodes.

The therapy titration module 314 can be programmed to control the neural stimulation according to stimulation instructions, such as a stimulation routine or schedule 318, stored in memory. Neural stimulation can be delivered in a stimulation burst, which is a train of stimulation pulses at a predetermined frequency. Stimulation bursts can be characterized by burst durations and burst intervals. A burst duration is the length of time that a burst lasts. A burst interval can be identified by the time between the start of successive bursts. A programmed pattern of bursts can include any combination of burst durations and burst intervals. A simple burst pattern with one burst duration and burst interval can continue periodically for a programmed period or can follow a more complicated schedule. The programmed pattern of bursts can be more complicated, composed of multiple burst durations and burst interval sequences. The programmed pattern of bursts can be characterized by a duty cycle, which refers to a repeating cycle of neural stimulation ON for a fixed time and neural stimulation OFF for a fixed time. Duty cycle is specified by the ON time and the cycle time, and thus can have units of ON time/cycle time. According to some embodiments, the control circuit controls the neural stimulation generated by the stimulation circuitry by initiating each pulse of the stimulation signal. In some embodiments, the stimulation control circuit initiates a stimulation signal pulse train, where the stimulation signal responds to a command from the controller circuitry by generating a train of pulses at a predetermined frequency and burst duration. The predetermined frequency and burst duration of the pulse train can be programmable. The pattern of pulses in the pulse train can be a simple burst pattern with one burst duration and burst interval or can follow a more complicated burst pattern with multiple burst durations and burst intervals. In some embodiments, the stimulation control circuit controls the stimulation output circuit to initiate a neural stimulation session and to terminate the neural stimulation session. The burst duration of the neural stimulation session under the control of the control circuit can be programmable. The controller may also terminate or override a neural stimulation session in response to an interrupt signal, such as may be generated by one or more sensed parameters or any other condition where it is determined to be desirable to stop neural stimulation.

A device may include a programmed therapy schedule or routine stored in memory and may further include a clock or timer which can be used to execute the programmable stimulation schedule. For example, a physician can program a daily/weekly schedule of therapy based on the time of day. A stimulation session can begin at a first programmed time, and can end at a second programmed time. Various embodiments initiate and/or terminate a stimulation session based on a signal triggered by a user. Various embodiments use sensed data to enable and/or disable a stimulation session. The stimulation schedule can be used to control the time intervals or period when the neural stimulation therapy is delivered. A schedule can be defined by a start time and an end time, or a start time and a duration. Various schedules deliver therapy periodically. By way of example and not limitation, a device can be programmed with a therapy schedule to deliver therapy from midnight to 2 AM every day, or to deliver therapy for one hour every six hours, or to deliver therapy for two hours per day, or according to a more complicated timetable. Various device embodiments apply the therapy according to the programmed schedule contingent on enabling conditions, such as sensed exercise periods, patient rest or sleep, a particular position/posture, low heart rate levels, and the like. For example, the stimulation can be synchronized to the cardiac cycle based on detected events that enable the stimulation. The therapy schedule can also specify how the stimulation is delivered.

Vagus nerve stimulation may cause dysphagia. Dysphagia is most commonly reported within the first 3 months after implantation of a vagus nerve stimulator, but may be experienced 12 months after implantation. The dysphagia may be directly related to the vagus nerve stimulation therapy. Various embodiments manage the vagus nerve stimulation for dysphagia until the patient accommodates to the vagus nerve stimulation and no longer experiences dysphagia. Some embodiments continually manage the vagus nerve stimulation for dysphagia.

Vagus nerve stimulation causes laryngeal muscle activation, which may disrupt the hyoid movement and laryngeal elevation when attempts to swallow are made. It is believed that the frequency and duration of the vagus nerve stimulation episodes ("stimulation ON") may correspond to likelihood of dysphagia.

Vagus nerve stimulation patients may experience cough increases after implantation of a vagus nerve stimulator. Cough increase is most commonly reported during the first 3 months after implantation, but may be experienced 12 months after implantation. Various embodiments manage the vagus nerve stimulation for cough increase until the patient accommodates to the vagus nerve stimulation and no longer experiences the increase in coughs. Some embodiments continually manage the vagus nerve stimulation for the increase in coughs.

Various embodiments suspend or delay or reduce vagus nerve stimulation upon swallow detection. Swallowing typically takes about one second to complete and people typically swallow once a minute. The swallowing rate may be higher during drinking or food consumption. Swallow avoidance is not expected to adversely affect the efficacy of the vagus nerve stimulation. These techniques have the potential to reduce the incidences of dysphagia, aspiration, aspiration pneumonia, laryngismus and increased cough, particularly in the first few months of VNS therapy.

Figure 4A:
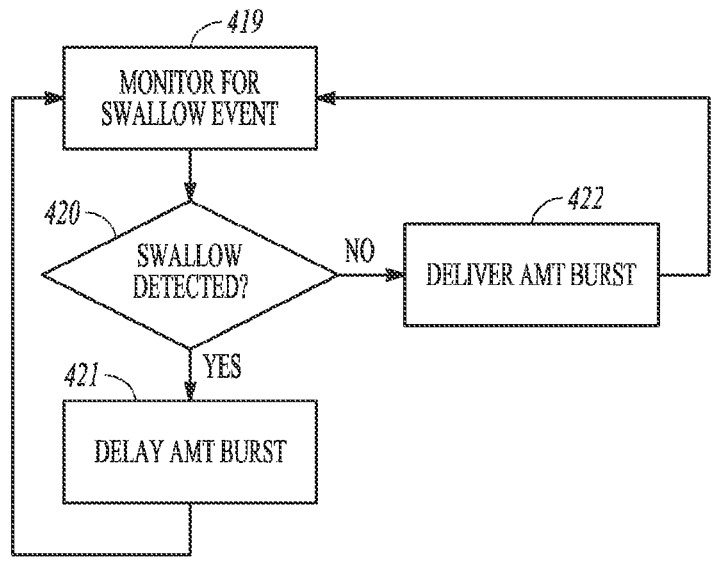
FIGS. 4A and 4B illustrate methods for managing autonomic modulation therapy (AMT), such as vagal stimulation therapy, to account for swallowing events.
Figure 4B:
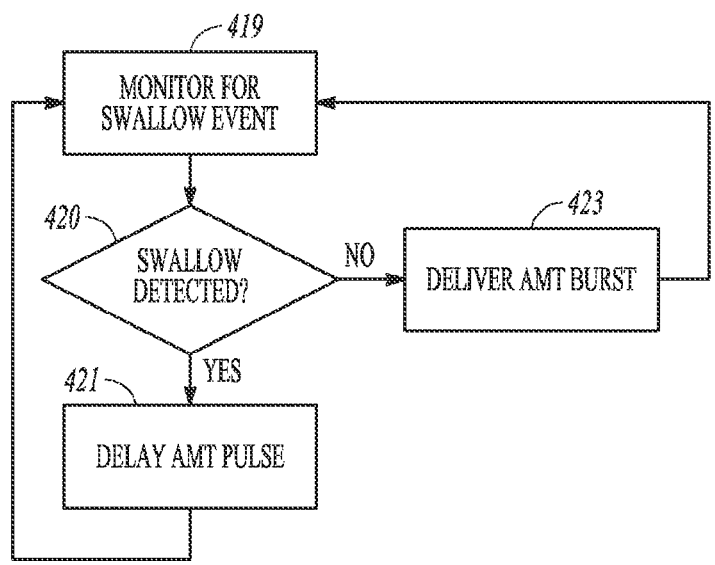

FIGS. 4A and 4B illustrate methods for managing autonomic modulation therapy (AMT), such as vagal stimulation therapy, to account for swallowing events. In both FIGS. 4A and 4B, the patient is monitored, using at least one sensed signal, for a swallow event 419 and it is determined if the swallow is detected at 420. In FIG. 4A, the AMT (e.g. vagus nerve stimulation) burst is delayed at 421 if a swallow was detected at 420 or is delivered at 422 if a swallow was not detected at 420. The burst includes a programmed series of pulses. In FIG. 4B, the AMT (e.g. vagus nerve stimulation) pulse (e.g. at least one of the pulses in a burst) is delayed at 421 if a swallow was detected at 420 or is delivered at 422 if a swallow was not detected at 420.

Various embodiments monitor for a swallow event during a time window prior to a scheduled burst of neural stimulation. If a swallow event does not occur, the entire stimulation burst is delivered. Some embodiments continue to monitor for a swallow event while the therapy is delivered. If the swallow event is detected during a burst (neural stimulation ON), the therapy is suspended mid-burst. Some embodiments are designed to account for the patient's accommodation to the stimulation. For example, some embodiments gradually shorten the detect window and/or delay window (over weeks, months, etc.). Some embodiments delay the stimulation burst if a swallowing event is detected. Some embodiments drop the scheduled stimulation burst if a swallowing event is detected, and resume the therapy with the next scheduled stimulation burst.

Figure 5A:
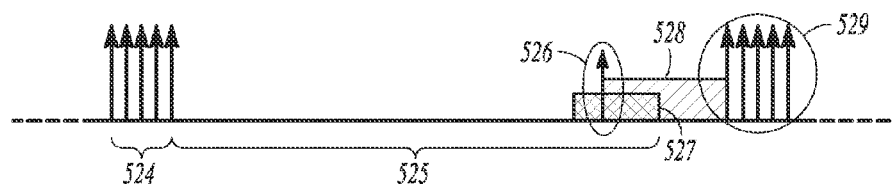
FIGS. 5A-5E illustrates some techniques for managing AMT in response to detected events, such as a detected swallowing event, detected dysphagia, detected laryngismus, detected pharyngitis, detected asthma, etc, according to various embodiments.
Figure 5B:
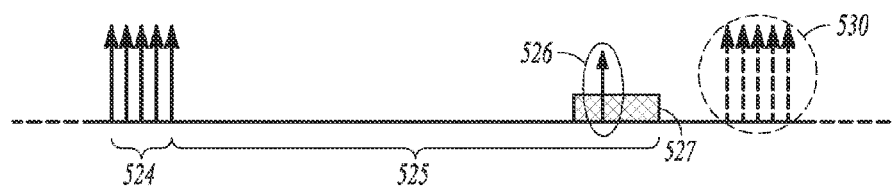
Figure 5C:
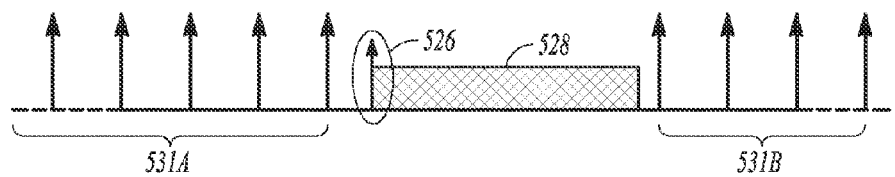
Figure 5D:
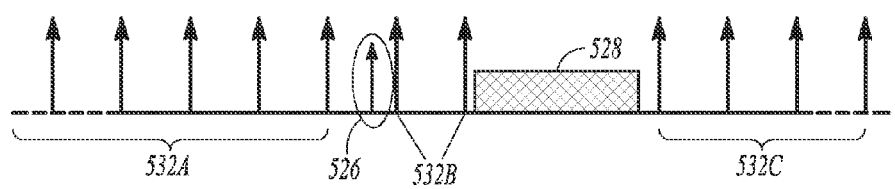
Figure 5E:
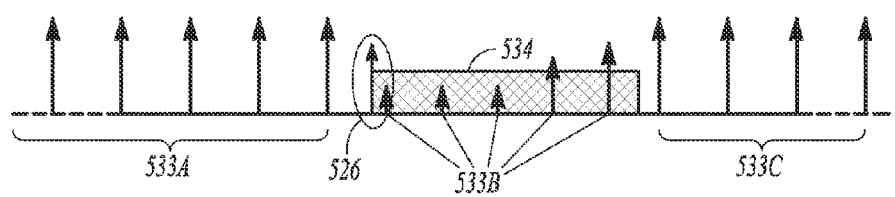

FIGS. 5A-5E illustrate some techniques for managing AMT in response to detected events, such as a detected swallowing event, detected dysphagia, detected laryngismus, detected pharyngitis, detected asthma, etc, according to various embodiments. In FIG. 5A, a stimulation burst 524 (AMT ON) is delivered followed by an AMT OH time 525. The end of the OFF time 525 includes a detect window 526. In the illustrated embodiment, the end of the AMT OFF period corresponds to the end of the detect window. If the event 527 is detected within the detect window 526, a delay time or delay window 528 occurs, after which the next scheduled AMT burst 529 is delivered. In FIG. 5B, a stimulation burst 524 is delivered followed by an OFF time 525. The end of the off time 525 includes a detect window 526. If the event is detected within the detect window, then the next scheduled AMT burst is not delivered, as generally illustrated at 530 with the broken lines where the burst would otherwise occur. According to some embodiments, the next scheduled AMT burst after the skipped burst is delivered. In FIG. 5C, a stimulation burst 531A is delivered. An event 526 is detected during the therapy burst. In response to the detected event, the stimulation burst is interrupted for a time, as is illustrated by the delay window 528. A timer can control the duration of the delay window. After the delay window, the stimulation burst 531B resumes for the AMT. In FIG. 5D, a stimulation burst 532A is delivered. An event 526 is detected during the therapy burst. In response to the detected event, the stimulation burst continues, as illustrated at 532B, for a programmed amount of time or for a programmed number of pulses in the burst. After which, the AMT burst is interrupted, as is illustrated by the delay window 528. A timer can control the duration of the delay window. After the delay window, the stimulation burst resumes, as illustrated at 532C, for the AMT. In FIG. 5E, a stimulation burst 533A is delivered. An event 526 is detected during the therapy burst. In response to the detected event, the stimulation burst is overridden for a time, as is illustrated by the therapy override window 534. A timer can control the duration of the override window. The override window is similar to the delay window. However, whereas stimulation is not delivered in the delay window, stimulation may be delivered within the override window. In the illustrated embodiment, the intensity of the AMT pulses (such as current amplitude, for example) in the burst is reduced (see 533B) during the override window. In some embodiments, as illustrated in FIG. 5E, the intensity of the AMT pulses steps down to a lower level for a programmed time or number of pulses, and then gradually increases until the end of the override window. After the delay window, the stimulation burst resumes, as illustrated at 533C, at the normal intensity for the AMT.

Figure 6A:
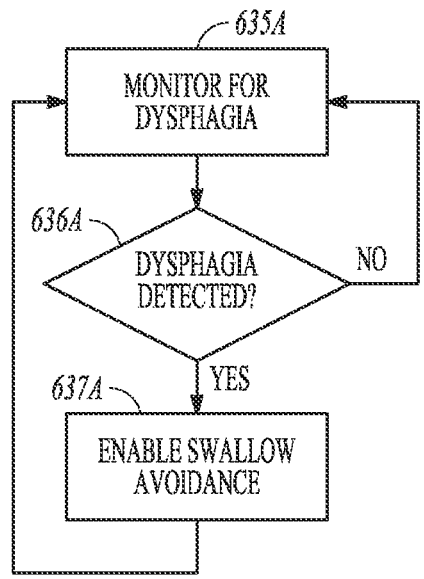
FIGS. 6A-6B illustrate some techniques for enabling a swallowing avoidance routine, according to various embodiments.
Figure 6B:
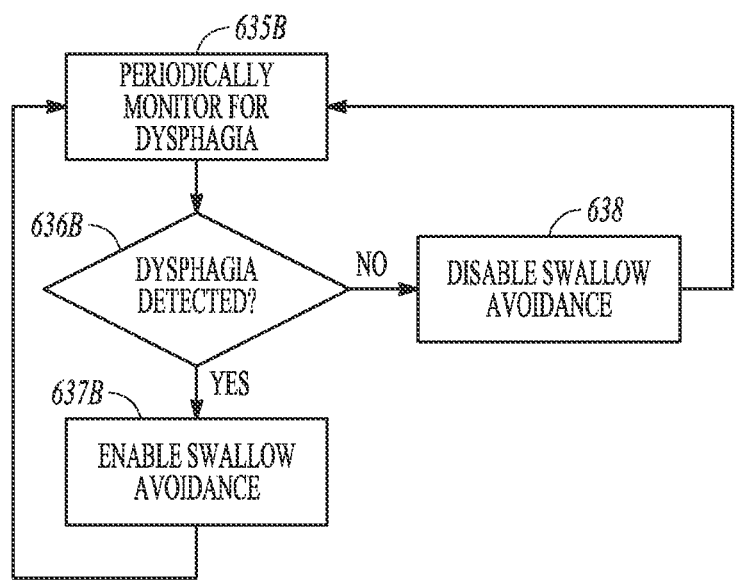

Some embodiments enable swallow avoidance algorithms if the patient is experiencing dysphagia. For example, the algorithm may be manually enabled by a physician or by a patient, or may be automatically enabled by a dysphagia detection algorithm. The dysphagia algorithm may be designed to periodically or intermittently search for dysphagia to determine whether the patient is experiencing dysphagia. FIGS. 6A-6B illustrate some techniques for enabling a swallowing avoidance routine, according to various embodiments. In the embodiment illustrated in FIG. 6A, a routine is implemented to monitor the patient for dysphagia 635A. If dysphagia is detected at 636A, the process implements a swallow avoidance routine 637A. In the embodiment illustrated in FIG. 6B, a routine is implemented to periodically (or intermittently according to a schedule) monitor for dysphagia 635B. If dysphagia is detected at 636B, the process implements a swallow avoidance routine 637B. If dysphagia is not detected at 636B, the routine disables the swallow avoidance routine 638.

Figure 7:
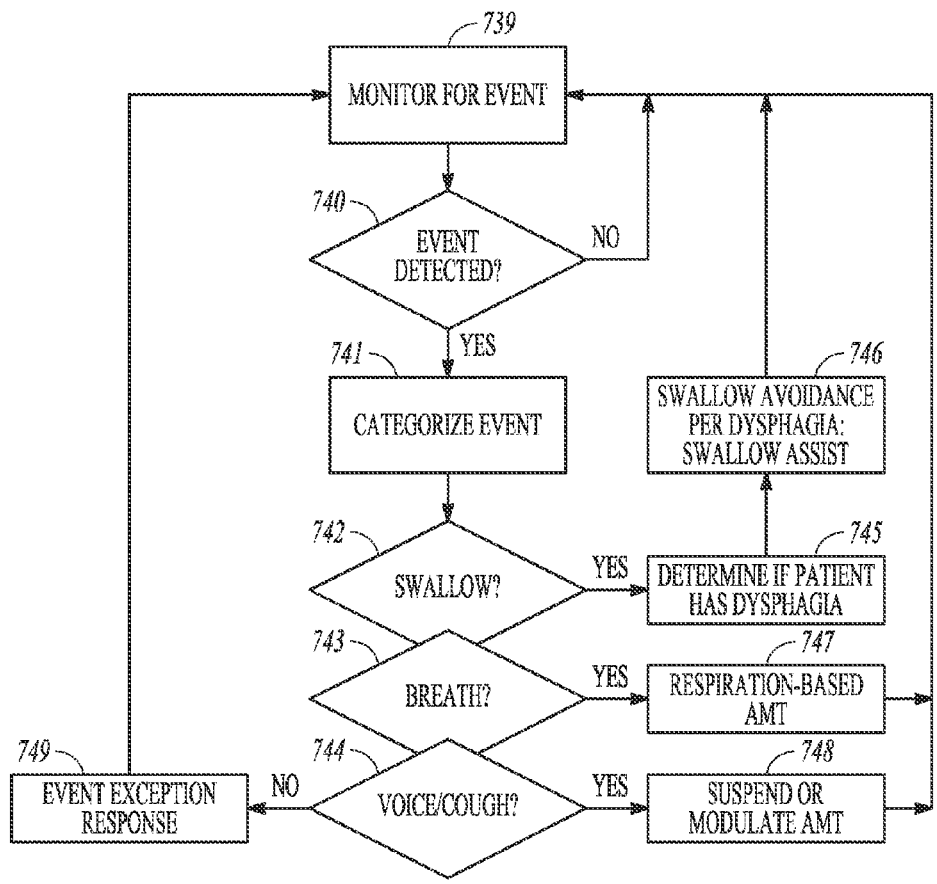
FIG. 7 illustrates an embodiment that categorizes a detected event as a swallowing event, a breathing event, a voice/cough event or another event, and that manages AMT according to the detected event.

FIG. 7 illustrates an embodiment that categorizes a detected event as a swallowing event, a breathing event, a voice/cough event or another event, and that manages AMT according to the detected event. The illustrated routine monitors the patient for an event at 739. If the event is detected at 740, the event is categorized 741 using the characteristics of the detected event. For example, the event can be categorized as a swallow event 742, or as a breath 743, or as a voice or cough event 744. If the detected event is categorized as a swallow event 742, the illustrated routine determines if the patient has dysphagia 745 and a process is performed to avoid swallowing for dysphagia to assist with swallowing 746. FIGS. 4-5 illustrate some processes to assist with avoiding swallowing. Some embodiments provide "swallow assist" to remove counterproductive effects of an AMT pulse during swallowing, A process to assist with swallowing is more complex, involving altering timing of AMT pulse to the portion of the second stage of swallowing where the upward and forward movement of the larynx naturally occurs. Alternatively, the amplitude of the AMT pulse could be increased during a swallow detect to ensure that the strength of the laryngeal muscle contraction is strong enough to seal the glottis even though the laryngeal muscle stimulation is lopsided (left vs. right). A more complex system could be developed that sequentially targets the muscle groups to mimic the normal sequence of muscle activations that occur during a swallow. If the detected event is categorized as a breath 743, the routine performs a process to monitor respiration and then alter AMT in response to respiration (see U.S. application Ser. No. 11/539,289, which is incorporated herein by reference in its entirety) or in response to apnea (e.g. U.S. Pat. No. 7,672, 728, which is incorporated herein by reference in its entirety). It is believed that a system can differentiate between different types of events using one common sensor. If the detected event is categorized as a voice/cough event, the routine performs a process to suspend or modulate the AMT 748 (see, for example, U.S. Pat. No. 5,205,285 for suppressing AMT when a voice is detected and U.S. application. Ser. No. 11/835,325 for cough detection, which are both incorporated herein by reference in their entirety). A system could differentiate between different types of events using one common sensor. If the detected event is not a swallow event, or a breath event, or a voice/cough event, the routine performs a process to perform an event exception 749. For example, the event exception response may be "do nothing" as the output of 740 could not be categorized. In an example, the event exception response temporarily suspends AMT because something was detected, event though the system was unable to categorize the event.

Various embodiments provide diagnostic functions that count the occurrences of each event by category, and various embodiments provide diagnostic functions based on whether stimulation was ON/OFF. For example, a difference in the the frequency of the events during ON vs. OFF may justify the need for the swallow avoidance algorithm to be turned ON by the physician, or to be "AUTO turned ON. Various embodiments provide diagnostic functions that track the number of times therapy was altered and sum total of the duration of time the therapy was suspended.

Some embodiments use an accelerometer to sense swallowing. The accelerometer may be on a lead, in a can, external on a neck, on a satellite sensor, etc. For example, the accelerometer may be used to detect motion or vibration. Some embodiments detect swallowing events using a microphone, an electromyograph (EMG) sensor, impedance sensors, or other sensors such as pressure sensor. Some embodiments use one swallow sensor. Some embodiments use more than one swallow sensor based on different technologies to provide a blended sensor. Correlations between the signals from the different sensor technologies can be used to validate a swallow event or to distinguish a type of event. EMG electrodes may be placed on the thyrohoyoid or mylohoyoid muscles. The thyrohoyoid is adjacent to internal jugular vein sheath and is readily accessible for EMG electrode implantation, as the neural stimulation lead is adjacent to the thyrohoyoid. The mylohoyoid is less accessible but an earlier indicator.

Vagus nerve stimulation may cause laryngismus. Laryngismus is most commonly reported within the first 3 months after implantation of a vagus nerve stimulator, but may be experienced 12 months after implantation. The laryngismus may be directly related to vagus nerve stimulation therapy. Various embodiments manage the vagus nerve stimulation for laryngismus until the patient accommodates to the vagus nerve stimulation and no longer experiences laryngismus. Some embodiments continually manage the vagus nerve stimulation for laryngismus.

Vagal nerve stimulation also results in laryngeal muscle activation, which may irritate the laryngeal cords or disrupt the muscle coordination during swallowing. Laryngismus typically lasts less than 60 seconds. Laryngismus causes a partial blocking of inhalation, while exhalation remains easier. Laryngismus may be triggered when the vocal cords or area below detects the entry of water, mucus, blood or other substance. Laryngismus is characterized by stridor (noisy high-pitched crowing sound) and/or retractions, and is typically seen in people who have silent reflux disease.

Various embodiments suspend or reduce amplitude/dosing of the vagus nerve stimulation if a laryngeal spasm is detected. Increased coughing, dysphagia, dyspnea and laryngismus in patients with vagal nerve stimulation may have related causes. Various embodiments temporarily suspend neural stimulation (e.g. for hours or days) if it is suspected that lamigismus is caused by irritation (a spontaneous event not tied to stimulation burst). Various embodiments temporarily suspend (e.g. for minutes or hours) if it is suspected that laryngismus is caused by aspiration (linked to stimulation burst—occurs during or just after AMT).

Some embodiments use one laryngismus sensor. Some embodiments use more than one laryngismus sensor based on different technologies to provide a blended sensor. Correlations between the signals from the different sensor technologies can be used to validate a laryngismus event or to distinguish a type of event. Some embodiments associate the vagus nerve stimulation to the laryngimus event to classify whether the laryngismus event is directly tied to the delivered vagus nerve stimulation.

Figure 8A:
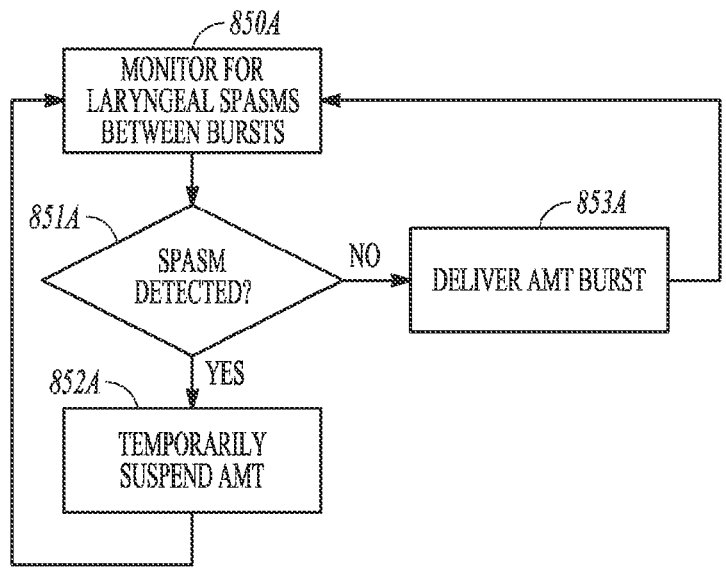
FIGS. 8A and 8B illustrate some techniques for managing AMT in response to detected laryngeal spasms.
Figure 8B:
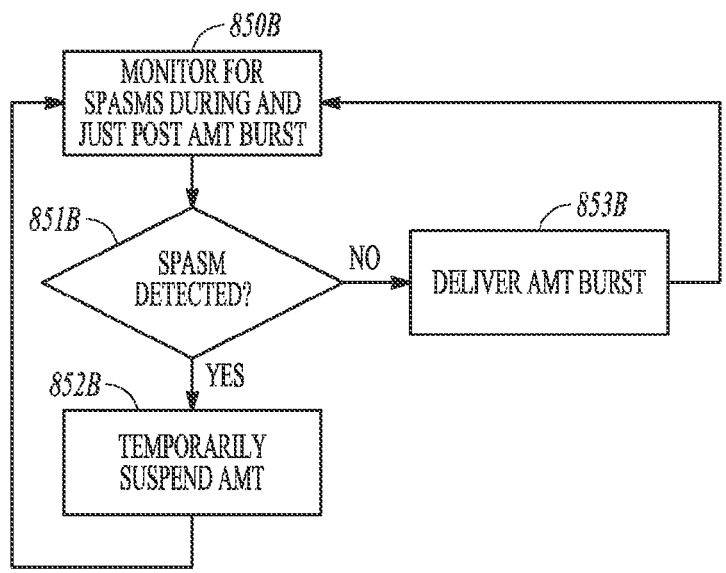

FIGS. 8A and 8B illustrate some techniques for managing AMT in response to detected laryngeal spasms. FIG. 8A illustrates an embodiment for detecting spontaneous laryngeal spasms and FIG. 8B illustrates an embodiment for detecting laryngeal spasms triggered by AMT bursts. In the embodiment illustrated in FIG. 8A, the patient is monitored for laryngeal spasms between scheduled, or programmed, AMT bursts 850A. If a laryngeal spasm is detected at 851A, the routine temporarily suspends the AMT 852A. If a laryngeal spasm is not detected at 851A, the routine delivers the scheduled AMT burst 853A. In the embodiment illustrated in FIG. 8B, the patient is monitored for laryngeal spasms during and just after a scheduled, or programmed, AMT burst 8509. The timing of the monitoring corresponds to the timing of spasms for spasms caused by the AMT. If a laryngeal spasm is detected at 8519, the routine temporarily suspends the AMT 852B. If a laryngeal spasm is not detected at 8519 during or just after the scheduled AMT burst, the routine delivers the next scheduled pulse or pulses 853B in the scheduled AMT burst. The response 852A or 852B may differ. For example, detected spasms in FIG. 8A imply that they were not triggered directly from the AMT stimulation and temporary suspension of therapy may be warranted to allow the muscles to "rest" or aspiration to clear, and detected spasms in FIG. 8B imply that the AMT stimulation is triggering the spasms and, particularly if there is a pattern where the spasms always occur during AMT stimulation, the response could be temporary suspension of AMT or altering amplitude, waveform, electrode vector, frequency, etc. in an attempt to avoid triggering further spasms.

Swallow avoidance itself may lead to reduced laryngismus as aspiration is a direct cause and swallow avoidance should reduce potential of aspiration. However, laryngismus may still occur even in the presence of swallow avoidance algorithms due to irritation resulting from stimulation of the recurrent laryngeal nerve, the ansa cervicalis or the levator veli palatini. Therefore, some embodiments still monitor for laryngeal spasms and react accordingly.

Some embodiments initially implement a short suspension time e.g. minutes/hours) if spasms are tied directly to the vagus nerve stimulation, but move to longer suspensions (e.g. hours/days) if more than one spasm is detected in a time period (e.g. day or week). Some embodiments require more than one spasm in a time period before temporarily suspending therapy. Some embodiments gradually shorten time of suspension over the months after implant as the patient accommodates (can shorten to 0 hours/days on that effectively would take 2 detected spasms to trigger suspension). Some embodiments shorten the time of suspension regardless whether triggered by spasm detection. If triggered, increase time of suspension and again gradually shorten time of suspension. Some embodiments fix the time of suspension if triggered multiple times.

The laryngeal spasm can be sensed using an accelerometer. The accelerometer may be on a lead, in or on a can, external on the neck, a satellite sensor, and the like. The accelerometer may be used to detect motion of vibration. Some embodiments use a microphone, EMG sensor, impedance sensor, or other sensor such as a pressure sensor to detect the spasm. Some embodiments use a minute ventilation sensor to detect laryngismus associated with disordered breathing.

Figure 9:
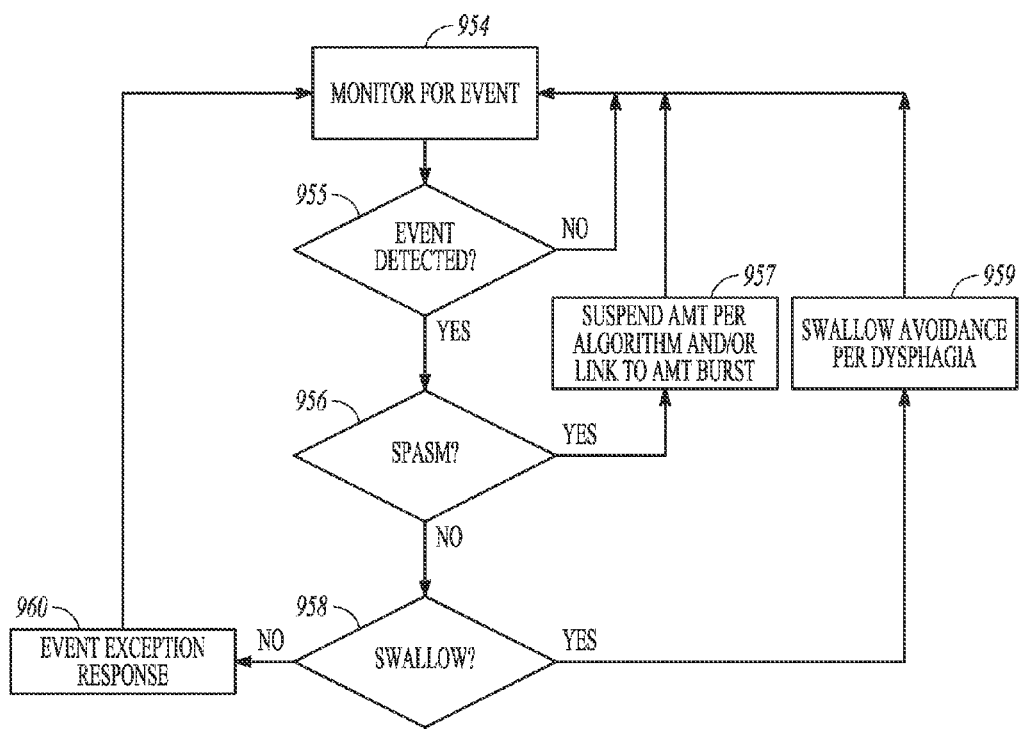
FIG. 9 illustrates an embodiment of a method for managing AMT in response to detected laryngeal spasms and swallowing events.

FIG. 9 illustrates an embodiment of a method for managing AMT in response to detected laryngeal spasms and swallowing events. In the illustrated routine, a patient is monitored for an event at 954. If an event is detected at 955 and the event is categorized as a laryngeal spasm at 956, the routine suspends AMT according to an algorithm and/or a link to an AMT burst 957. If an event is detected at 955 and the event is categorized as a swallow at 958, the routine delivers AMT in a manner that avoids delivering stimulation during the swallow event, as discussed with respect to dysphagia 959. If an event is detected at 955 hut the event is neither a spasm or a swallow, the routine enters an event exception response 960 For example, the event exception response may be "do nothing" as the output could not be categorized. For some embodiments, the event exception response temporarily suspends AMT because something was detected, even though the system was unable to categorize the event. The response may be prophylactic temporary suspension of AMT or with no response other than tracking the suspension(s) by counting the number of suspensions and/or the sum total of the duration of the suspension(s).

Figure 10:
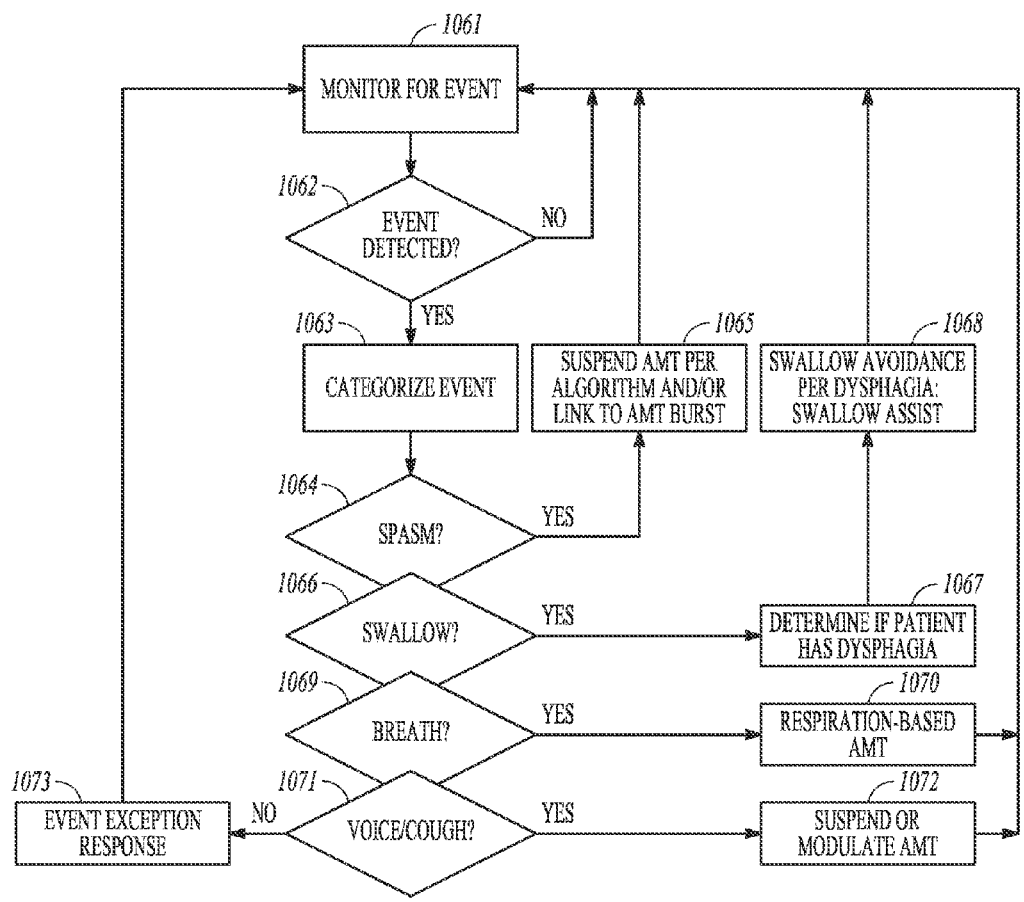
FIG. 10 illustrates an embodiment of a method for managing AMT in response to detected laryngeal spasms, swallowing events, breathing events, and voice/cough events.

FIG. 10 illustrates an embodiment of a method for managing AMT in response to detected laryngeal spasms, swallowing events, breathing events, and voice/cough events. In the illustrated routine, a patient is monitored for an event at 1061. If an event is detected at 1062, the detected event is categorized at 1063. If a detected event is categorized as a laryngeal spasm at 1064, the routine suspends AMT according to an algorithm and/or a link to an AMT burst 1065. If a detected event is categorized as a swallow 1066, the routine responds to the swallow event by determining if the patient has dysphagia 1067 and temporarily performing a routine to deliver AMT a manner that avoids delivering stimulation during the swallow event, as discussed with respect to dysphagia 1068, to assist with swallowing. If a detected event is categorized as a breath 1069, the routine temporarily performs a respiration based AMT 1070 in response to the breath event. If a detected event is categorized as a voice event or cough event 1071, the routine temporarily suspends or modulates the AMT 1072 in response to the cough event. If an event is detected at 1062 but the event is not a spasm, swallow, breath, voice or cough, the routine enters an event exception response 1073. For example, the event exception response may be "do nothing" as the output could not be categorized. In an example, the event exception response temporarily suspends AMT because something was detected, event though the system was unable to categorize the event. The response may be prophylactic temporary suspension of AMT or with no response other than tracking the suspension(s) by counting the number of suspensions and/or the sum total of the duration of the suspension(s).

Various embodiments suspend or reduce amplitude/dosing of the vagus nerve stimulation if pharyngitis is detected. Pharyngitis may be the result of increased coughing due to aspiration or the result of irritation from food or liquid entering the nasopharynx. Both conditions may be caused by the vagus nerve stimulation if the stimulation compromises the muscle coordination necessary for swallowing. Swallow avoidance may lead to reduced pharyngitis for these reasons.

Pharyngitis may be detectable by monitoring swallow patterns in addition to the monitoring for inflammation. Swallow patterns will change with a swollen sore pharynx because of discomfort. A single swallow may become lengthened in duration, or the timing between muscle group activation may change, as the individual attempts to control the pain associated with pharyngitis. In addition, the discomfort associated with pharyngitis may result in fewer swallows or rapid grouped swallows followed by a cessation of swallowing for a period of time as the individual attempts to control the pain associated with pharyngitis.

Vagal nerve stimulation has anti-inflammatory properties and altering the delivery of VNS or AMT may help in recovery from pharyngitis. Some patients may not typically present with pharyngitis, but only on occasion show signs of pharyngitis with accompanying inflammatory markers like temperature. To accommodate such patients, some embodiments wait until the rise in temperature (fever) or other accompanying inflammatory marker subsides to perform pharyngitis avoidance.

The onset of an asthmatic event can be detected by monitoring breathing or trachea sounds for the distinct sound patterns associated with asthma, rales, or rhonchus. Some embodiments suspend or reduce amplitude/dosing of VNS if asthma is detected. However, vagal nerve stimulation has anti-inflammatory properties. As such, it may be desirable to alter, rather than suspend or reduce, the delivery of VNS or AMT in the presence of an asthmatic event.

Pharyngitus is most commonly reported within the first 3 months after implantation of a vagus stimulation device, but may be experienced 12 months after implantation. The pharyngitus may be directly related to therapy. Various embodiments manage the vagus nerve stimulation for pharyngitus until the patient accommodates to the vagus nerve stimulation and no longer experiences pharyngitus. Some embodiments continually manage the vagus nerve stimulation for pharyngitus.

Asthma may be exacerbated by the vagus nerve stimulation. This may be the result of irritation from the vagus nerve stimulation, or the result of increased coughing, dysphagia, dyspnea or laryngismus associated with vagus nerve stimulation. A sore throat, in and of itself, is not a significant concern, but should be monitored as swelling can obstruct breathing. Heart failure patients already have comprised breathing.

Various embodiments temporarily suspend for hours or days if it is suspected that pharyngitis is caused by irritation from AMT. Various embodiments temporarily suspend for minutes or hours if an asthma attack is detected.

Figure 11A:
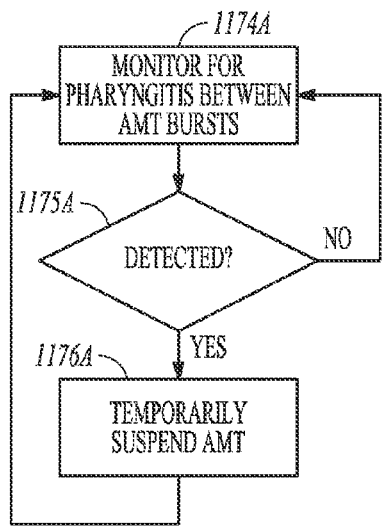
FIGS. 11A-11C illustrate some techniques for managing AMT in response to pharyngitis, increased inflammation and breaths.
Figure 11B:
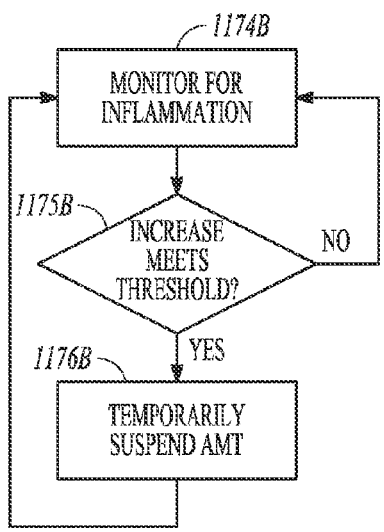
Figure 11C:
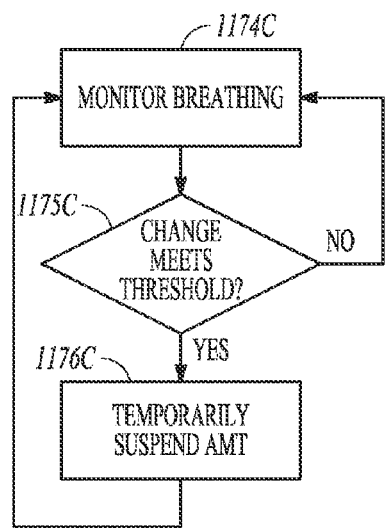

FIGS. 11A-11C illustrate some techniques for managing AMT in response to pharyngitis, increased inflammation and breaths. In the embodiment for managing AMT in response to pharyngitis illustrated in FIG. 11A, a patient is monitored for pharyngitis between AMT bursts 1174A. If pharyngitis is detected at 1175A the AMT is temporarily suspended 1176A. In the embodiment for managing AMT in response to inflammation illustrated in FIG. 11B, a patient is monitored for inflammation 1174B. If inflammation is detected at 1175B the AMT is temporarily suspended 1176B. In the embodiment for managing AMT in response to breaths illustrated in FIG. 11C, a patient is monitored for breathing 1174C. If a breath is detected at 1175C the AMT is temporarily suspended. 1176C.

Pharyngitis may be sensed using various technologies. For example, inflammation may be detected by monitoring impedance near electrodes using larger vectors or by monitoring impedance across the throat. The measurement frequency for pharyngitis can be relatively low (minutes, hourly, daily, etc.). As pharyngitis can lead to swelling that obstructs breathing, the breathing pattern will change, which can be detected with minute ventilation. Some embodiments use an accelerometer or acoustic microphone to sense turbulence or an increase in raspiness.

Some embodiments use one pharyngitis sensor. Some embodiments use more than one pharyngitis sensor based on different technologies to provide a blended sensor. Correlations between the signals from the different sensor technologies can be used to validate a pharyngitis event or to distinguish a type of event. Some embodiments associate the vagus nerve stimulation to the pharyngitis event to classify whether the pharyngitis event is directly tied to the delivered vagus nerve stimulation. Asthma can be distinguished from pharyngitis by rapid onset.

The algorithms for managing vagal nerve stimulation for dysphagia, laryngismus, pharyngitis and asthma can be blended. Swallow avoidance is the main technique/algorithm in the hopes that doing so reduces the occurrence of dysphagia, laryngismus, pharyngitis and cough. Swallow avoidance is not needed if therapy is temporarily suspended in response to detected laryngismus, pharyngitis or asthmatic event. Swallow avoidance still occurs if the response is a reduction of amplitude/dosing or if the delivery is altered due to one of those detections. This can also be extended to include blending with algorithms related to managing vagal nerve stimulation for voice detection or apnea detection.

Figure 12A:
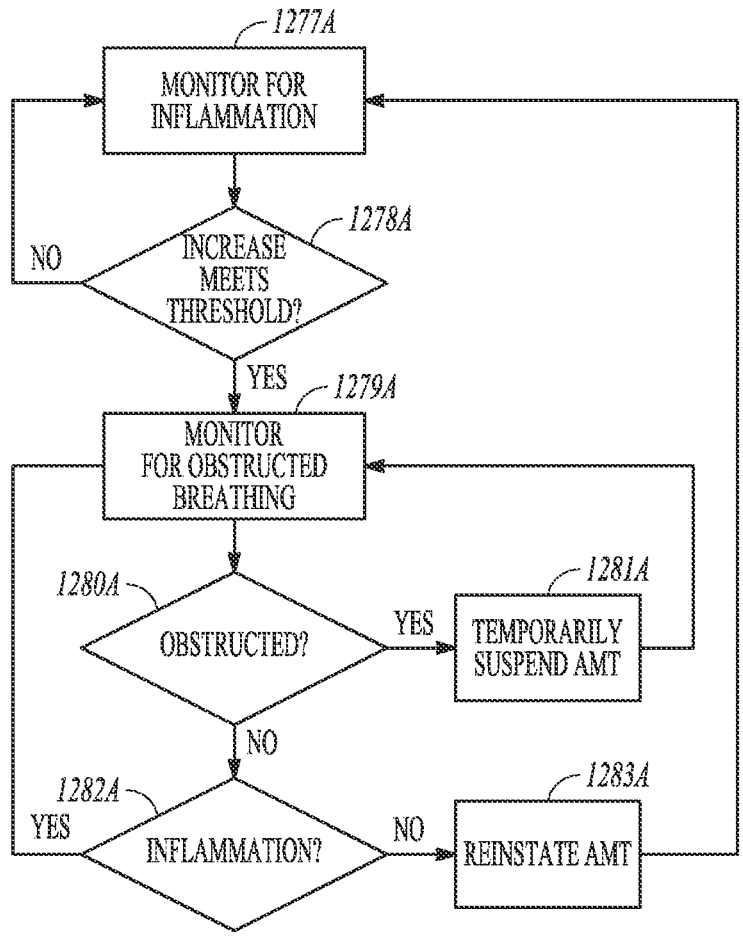
FIGS. 12A-12B illustrate some techniques for managing AMT in response to monitored inflammation, raspiness or turbulence.
Figure 12B:
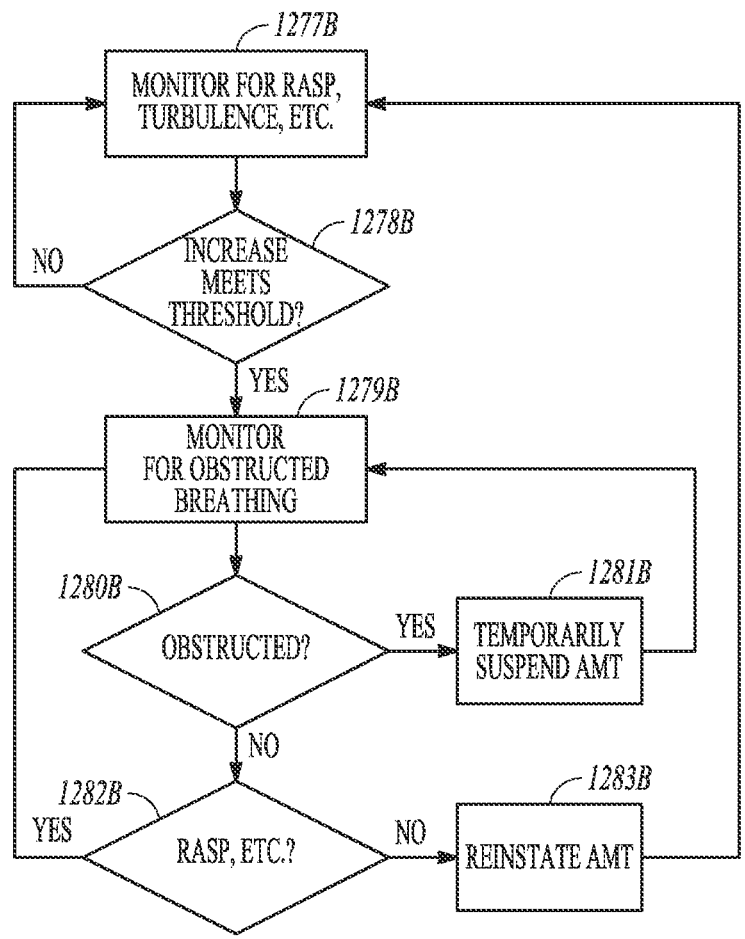

FIGS. 12A-12B illustrate some techniques for managing AMT in response to monitored inflammation, raspiness or turbulence. In the embodiment illustrated in FIG. 12A, a patient is monitored for inflammation at 1277A. If the detected inflammation satisfies a threshold value for the inflammation 1278A, the system enables a routine to monitor the patient for obstructed breathing 1279A. If breathing is obstructed 1280A, the routine temporarily suspends AMT 1281A. If breathing is not obstructed at 1280A and if inflammation is detected at 1282A, the system continues to monitor the patient for obstructed breathing 1279A. If the inflammation has been significantly reduced or eliminated, the routine reinstates the AMT 1283A and monitors for inflammation 1277A. In the embodiment illustrated in FIG. 12B, a patient is monitored for raspiness or turbulence, for example, at 12779. If the detected condition satisfies a threshold value 1278B, the system enables a routine to monitor the patient for obstructed breathing 1279B. If breathing is obstructed 1280B, the routine temporarily suspends AMT 12819. If breathing is not obstructed at 1280B and if the detected condition (raspiness, etc.) remains 1282B, the system continues to monitor the patient for obstructed breathing 1279B. If the detected condition (raspiness, etc.) has been significantly reduced or eliminated, the routine reinstates the AMT 1283B and monitors for the condition (raspiness, turbulence etc.) 1277B.

Figure 13A:
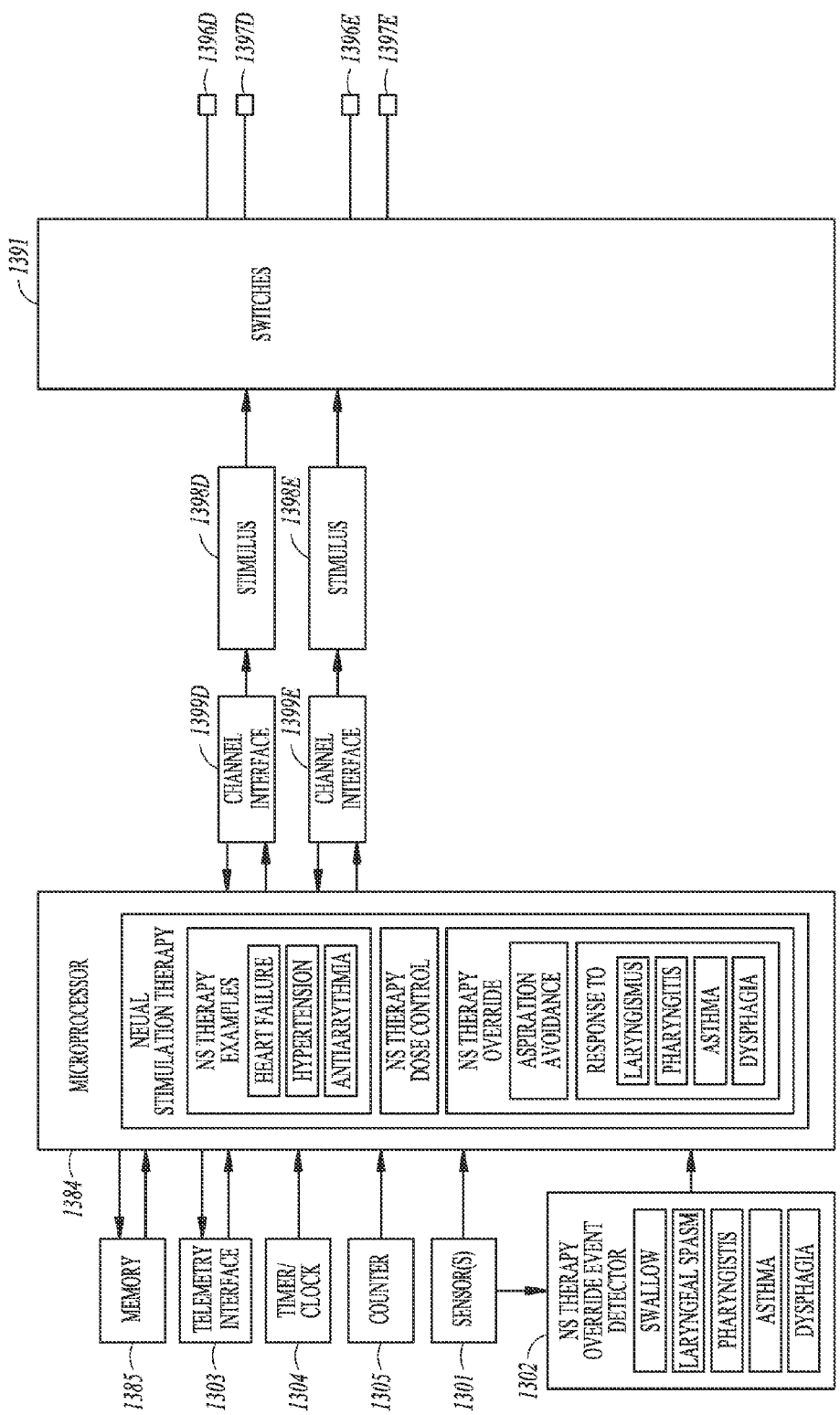
FIGS. 13A and 13B illustrate system diagrams of a microprocessor-based implantable device, according to various embodiments.
Figure 13B:
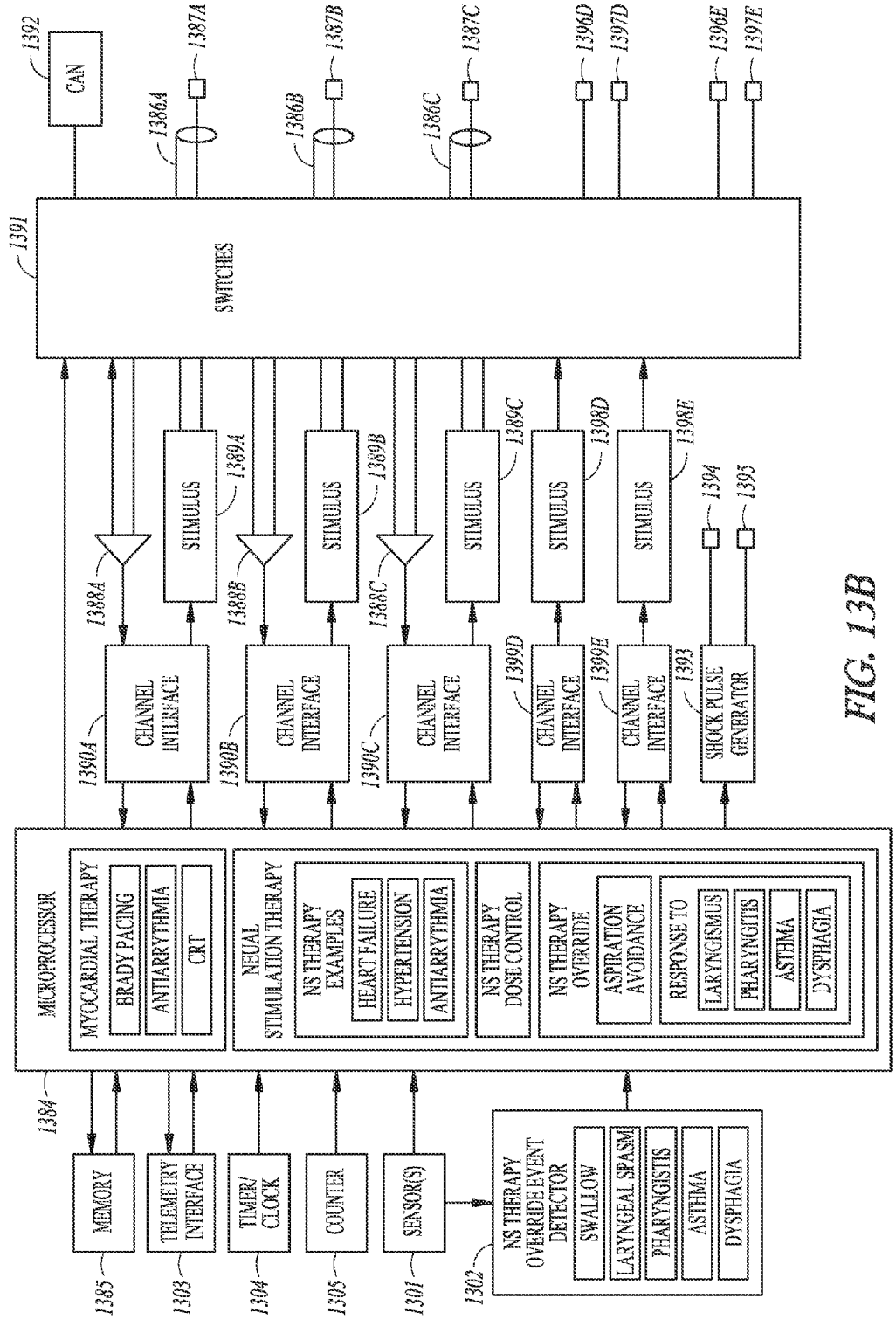

FIGS. 13A and 13B illustrate system diagrams of a microprocessor-based implantable device, according to various embodiments. FIG. 13A illustrates an embodiment of an implantable neural stimulation device, and FIG. 13B illustrates an embodiment of an implantable device configured to deliver both neural stimulation as well as myocardial stimulation for a cardiac rhythm management (CRM) therapy.

With reference to FIG. 13B, the controller of the device is a microprocessor 1384 which communicates with a memory 1385 via a bidirectional data bus. The controller could be implemented by other types of logic circuitry (e.g., discrete components or programmable logic arrays) using astute machine type of design. As used herein, the term "circuitry" should be taken to refer to either discrete logic circuitry or to the programming of a microprocessor and combinations thereof. Shown in the figure are three examples of sensing and pacing channels designated "A" through "C" comprising bipolar leads with ring electrodes 1386A-C and tip electrodes 1387A-C, sensing amplifiers 1388A-C, pacing stimuli 1389A-C, and channel interfaces 1390A-C. Each channel thus includes a pacing channel made up of the pulse generator connected to the electrode(s) and a sensing channel made up of the sense amplifier connected to the electrode(s). The channel interfaces 1390A-C communicate bidirectionally with the microprocessor 1384, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias. The electrodes of each bipolar lead are connected via conductors within the lead to a switching network 1391 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing (can) 1392 or an electrode on another lead serving as a ground electrode. A shock pulse generator 1393 is also interfaced to the controller for delivering a defibrillation shock via shock electrodes (e.g. electrodes 1394 and 1395) to the atria or ventricles upon detection of a shockable tachyarrhythmia.

With reference to both FIGS. 13A and 13B, neural stimulation channels, identified as channels D and E, are incorporated into the device for delivering parasympathetic stimulation and/or sympathetic inhibition, where one channel includes a bipolar lead with a first electrode 1396D and a second electrode 1397D, a pacing stimulus 1398D, and a channel interface 1399D, and the other channel includes a bipolar lead with a first electrode 1396E and a second electrode 1397E, a pacing stimulus 1398E, and a channel interface 1399E. Other embodiments may use unipolar leads in which case the neural stimulation pulses are referenced to the can or another electrode. Other embodiments may use tripolar or multipolar leads. In various embodiments, the pulse generator for each channel outputs a train of neural stimulation pulses which may be varied by the controller as to amplitude, pulse-width, frequency, duty-cycle, and the like. A programmed schedule in the memory can be used to deliver intermittent neural stimulation (AMT) with a plurality of neural stimulation bursts (stimulation ON) separated by time without stimulation (stimulation OFF) and where each burst includes a plurality of pulses. In some embodiments, each of the neural stimulation channels uses a lead which can be intravascularly disposed near an appropriate neural target. Other types of leads and/or electrodes, such as subcutaneous leads and electrodes implanted in the carotid sheath, may also be employed. In some embodiments, the leads of the neural stimulation electrodes are replaced by wireless links.

Sensor(s) 1301 are used by the microprocessor to control therapy. For example, sensor(s) can be used to determine capture (e.g. laryngeal vibrations), the efficacy of therapy (e.g. heart rate, blood pressure) and/or detect events (e.g. cough) or states (e.g. activity sensors). Sensor(s) 1301 can include sensor(s) to detect physiological parameters analyzed and categorized by a neural stimulation override event detector 1302 to determine if one or more events occur for which it is desired to override the programmed neural stimulation therapy. The event detector 1302 is configured to analyze characteristics of the signal(s) generated by the sensor's) to determine if the detected event has occurred. Examples of detectable events include swallow events, laryngeal spasm events, pharyngitis, asthma and dysphagia.

The figure illustrates a telemetry interface 1303 connected to the microprocessor, which can be used to communicate with an external device. Some embodiments use a timer/clock 1304 and/or a counter 1305, such as may be used to time the pulses and bursts of stimulation delivered by the device. The counter may count sensed events such as heart rate and stimulation pulses and/or event(s) that may trigger an override such as swallows and episodes of laryngeal spasms, pharyngitis, asthma, and dysphagia.

NS therapy routines also include routines or algorithms as described in this document. Examples of myocardial therapy routines include bradycardia pacing therapies, anti-tachycardia shock therapies such as cardioversion or defibrillation therapies, anti-tachycardia pacing therapies (ATP), and cardiac resynchronization therapies (CRT). Examples of NS therapy routines also include VST therapies to provide chronic therapies for chronic conditions such as heart failure therapies and hypertension therapies and to provide more acute therapies for acute conditions such as various anti-arrhythmia therapies. Other neural stimulation of autonomic nerve targets may be incorporated. The neural stimulation therapy routines may also include a neural stimulation therapy dose control routine, according to various embodiments, to ensure that a desired dose of stimulation (e.g. average stimulation pulses/time period) is delivered, even if the scheduled stimulation schedule is overridden. The neural stimulation routines also include various routine(s) and combinations thereof to override the scheduled neural stimulation in response to one of the detected events detected by the event detector 1302. These routine(s) can override the scheduled neural stimulation therapy to provide a desired response to detected laryngismus, or to detected pharyngitis, or to detected asthma, or to detected dysphagia, or various combinations thereof. These routine(s) may include routines to avoid aspiration in response to an event detected by the neural stimulation therapy override event detector 1302. Examples of these routines have been discussed above (e.g. FIG. 4A to FIG. 12B and corresponding portions of the description). Various embodiments include any one or any combination of two or more of these routines.

Figure 14A:
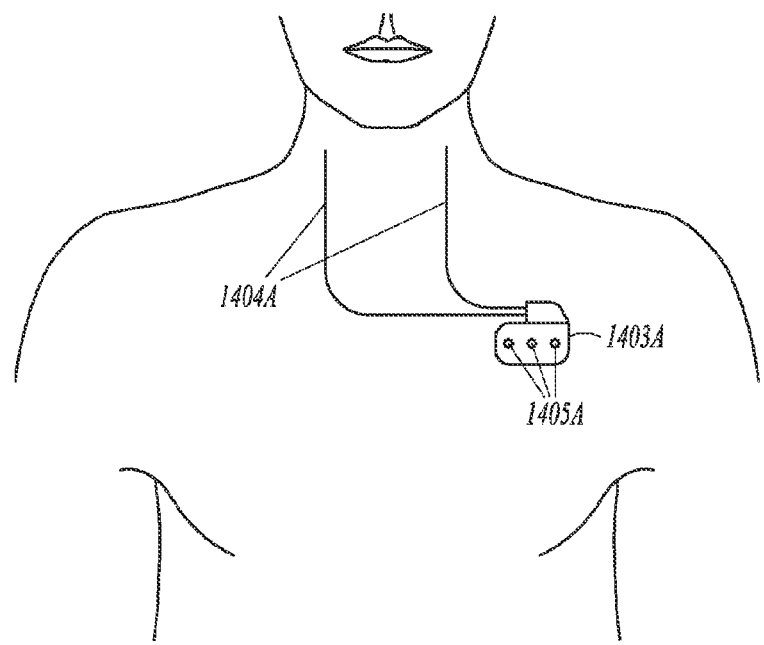
FIGS. 14A-14B illustrate system embodiments adapted to provide AMT, and are illustrated as bilateral systems that can stimulate both the left and right vagus nerve.
Figure 14B:
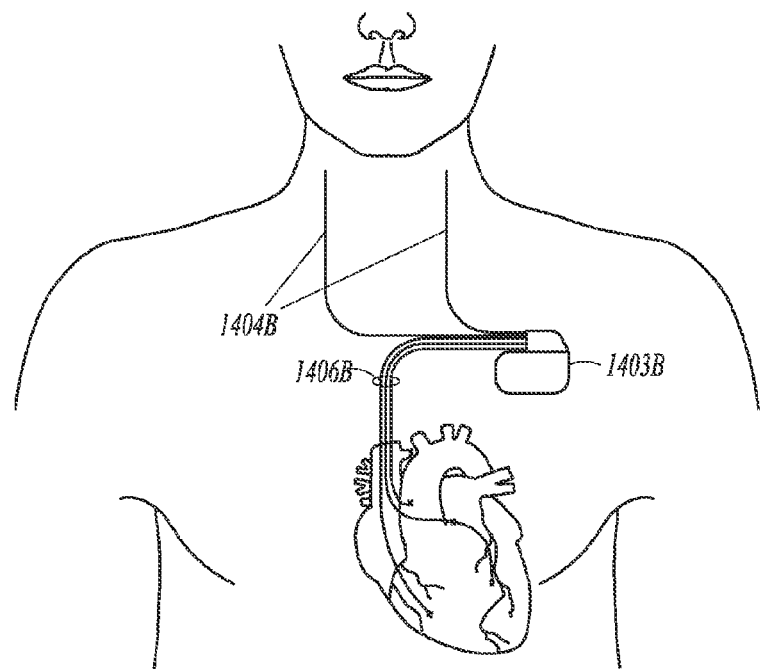

FIGS. 14A-14B illustrate system embodiments adapted to provide VST, and are illustrated as bilateral systems that can stimulate both the left and right vagus nerve. Those of ordinary skill in the art will understand, upon reading and comprehending this disclosure, that systems can be designed to stimulate only the right vagus nerve, systems can be designed to stimulate only the left vagus nerve, and systems can be designed to bilaterally stimulate both the right and left vagus nerves. The systems can be designed to stimulate nerve traffic (providing a parasympathetic response when the vagus is stimulated), or to inhibit nerve traffic (providing a sympathetic response when the vagus is inhibited). Various embodiments deliver unidirectional stimulation or selective stimulation of some of the nerve fibers in the nerve. FIGS. 14A-14B illustrate the use of a lead to stimulate the vagus nerve. Wireless technology could be substituted for the leads, such that a leadless electrode is adapted to stimulate a vagus nerve and is further adapted to wirelessly communicate with an implantable system for use in controlling the VST.

FIG. 14A illustrates a system embodiment in which an IMD 1403A is placed subcutaneously or submuscularly in a patient's chest with lead(s) 1404A positioned to stimulate vagus nerve. According to various embodiments, neural stimulation lead(s) 1404A are subcutaneously tunneled to a neural target, and can have a nerve cuff electrode to stimulate the neural target. Some vagus nerve stimulation lead embodiments are intravascularly fed into a vessel proximate to the neural target, and use electrode(s) within the vessel to transvascularly stimulate the neural target. For example, some embodiments stimulate the vagus using electrode(s) positioned within the internal jugular vein. Other embodiments deliver neural stimulation to the neural target from the internal jugular vein, or the subclavian vein. The neural targets can be stimulated using other energy waveforms, such as ultrasound and light energy waveforms. The illustrated system includes leadless ECG electrodes 1405A on the housing of the device. These ECO electrodes are capable of being used to detect heart rate, for example.

FIG. 14B illustrates an IMD 1403B placed subcutaneously or submuscularly in a patient's chest with lead(s) 1406B positioned to provide a CRM therapy to a heart, and with lead(s) 1404B positioned to stimulate and/or inhibit neural traffic at a neural target, such as a vagus nerve, according to various embodiments. According to various embodiments, neural stimulation lead(s) are subcutaneously tunneled to a neural target, and can have a nerve cuff electrode to stimulate the neural target. Some lead embodiments are intravascularly fed into a vessel proximate to the neural target, and use transducer(s) within the vessel to transvascularly stimulate the neural target. For example, some embodiments target the vagus nerve using electrode(s) positioned within the internal jugular vein.

Figure 15:
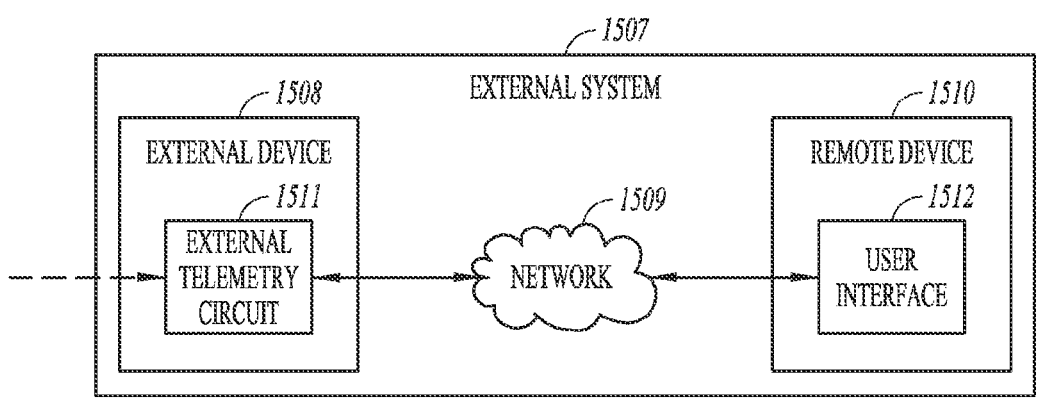
FIG. 15 is a block diagram illustrating an embodiment of an external system.

FIG. 15 is a block diagram illustrating an embodiment of an external system 1507. The external system includes a programmer, in some embodiments. In the illustrated embodiment, the external system includes a patient management system. As illustrated, the external system is a patient management system including an external device 1508, a telecommunication network 1509, and a remote device 1510. The external device 1508 is placed within the vicinity of an implantable medical device (MID) and includes an external telemetry system 1511 to communicate with the IMD. The remote device(s) is in one or more remote locations and communicates with the external device through the network, thus allowing a physician or other caregiver to monitor and treat a patient from a distant location and/or allowing access to various treatment resources from the one or more remote locations. The illustrated remote device includes a user interface 1512. According to various embodiments, the external device includes a neural stimulator, a programmer or other device such as a computer, a personal data assistant or phone. The external device, in various embodiments, includes two devices adapted to communicate with each other over an appropriate communication channel, such as a computer by way of example and not limitation. The external device can be used by the patient or physician to provide feedback indicative of patient discomfort, for example.

As will be understood by one of ordinary skill in the art upon reading and comprehending the present subject matter, various embodiments of the present subject matter improve the ability to quickly and accurately implant and program a neural stimulation system and intermittently reprogram the system, improve patient acceptance of therapy and maintain efficacious levels of therapy. The modules and other circuitry shown and described herein can be implemented using software, hardware, firmware and combinations thereof.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. An implantable device, comprising:
a neural stimulation circuit configured to deliver an autonomic modulation therapy (AMT) to treat a disease, including deliver neural stimulation to an autonomic neural target according to a programmed schedule for the AMT;
an event detector configured to detect at least one event, wherein the event detector is configured to detect at least one of a swallow event, a laryngeal spasm event, a pharyngitis event, an asthma event, or a dysphagia event,
wherein the neural stimulation circuit includes a therapy override controller configured to respond to a detected event, detected by the event detector, and override the programmed schedule for delivering neural stimulation for the AMT, and
wherein the neural stimulation circuit is configured to deliver intermittent neural stimulation with programmed bursts of neural stimulation pulses, wherein each programmed burst is a stimulation ON time separated from adjacent bursts in the programmed schedule by a stimulation OFF time.

2. The device of claim 1, wherein the therapy override controller is configured to override the programmed schedule to avoid aspiration.

3. The device of claim 1, wherein the therapy override controller is configured to override the programmed schedule to manage the neural stimulation for laryngismus.

4. The device of claim 1, wherein the therapy override controller is configured to override the programmed schedule to manage the neural stimulation for asthma.

5. The device of claim 1, wherein the therapy override controller is configured to override the programmed schedule to manage the neural stimulation for dysphagia.

6. The device of claim 1, wherein the therapy override controller is configured to override the programmed schedule by delaying a subsequent burst of neural stimulation pulses after the event detector detects the event.

7. The device of claim 1, wherein the therapy override controller is configured to delay a neural stimulation pulse in the programmed burst when the event detector detects the event within the burst.

8. The device of claim 1, wherein the therapy override controller is configured to skip a subsequent programmed burst of neural stimulation pulses if the swallow event occurs in a detect window of time within the stimulation OFF time.

9. The device of claim 1, wherein the therapy override controller is configured to interrupt a burst for an override time period when the event detector detects the event within the burst, and resume the burst after the override time period.

10. The device of claim 1, wherein the therapy override controller is configured to continue the burst for one or more pulses after the event detector detects the event within the burst, and then interrupt the burst for an override time period, and resume the burst after the override time period.

11. An implantable device, comprising:
a neural stimulation circuit configured to deliver an autonomic modulation therapy (AMT) to treat a disease, including deliver neural stimulation to an autonomic neural target according to a programmed schedule for the AMT;
an event detector configured to detect a swallow event,
wherein the neural stimulation circuit includes a therapy override controller configured to respond to a detected swallow event, detected by the event detector, and override the programmed schedule for delivering neural stimulation for the AMT, and
wherein the neural stimulation circuit is configured to deliver intermittent neural stimulation with programmed bursts of neural stimulation pulses, wherein each programmed burst is a stimulation ON time separated from adjacent bursts in the programmed schedule by a stimulation OFF time.

12. The device of claim 11, wherein:
the event detector is configured to detect the swallow event during a programmed burst of neural stimulation pulses, and the therapy override controller is configured to delay a neural stimulation pulse in the programmed burst.

13. The device of claim 11, wherein:
the therapy override controller is configured to skip a subsequent programmed burst of neural stimulation pulses if the swallow event occurs in a detect window of time within the stimulation OFF time.

14. The device of claim 11, wherein:
the event detector is configured to detect the swallow event during a programmed burst of neural stimulation pulses, and the therapy override controller is configured to interrupt the burst for an override time period, and resume the burst after the override time period.

15. The device of claim 11, wherein:
the event detector is configured to detect the swallow event during a programmed burst of neural stimulation pulses, and the therapy override controller is configured to continue the burst for one or more pulses, and then interrupt the burst for an override time period, and resume the burst after the override time period.

16. An implantable device, comprising:
a neural stimulation circuit configured to deliver an autonomic modulation therapy (AMT) to treat a disease, including deliver neural stimulation according to a programmed schedule;
an event detector configured to detect a dysphagia event,
wherein the neural stimulation circuit includes a therapy override controller configured to respond to a detected dysphagia event, detected by the event detector, and override the programmed schedule for the AMT, wherein the therapy override controller is configured to implement a swallow override routine in response to the detected dysphagia event, and
wherein the neural stimulation circuit is configured to deliver intermittent neural stimulation with programmed bursts of neural stimulation pulses, wherein each programmed burst is a stimulation ON time separated from adjacent bursts in the programmed schedule by a stimulation OFF time.

17. The device of claim 16, wherein in implementing the swallow override routine, the therapy override controller is configured to detect a swallow event and respond to the detected swallow event by overriding the programmed schedule.

18. The device of claim 17, wherein the device is configured to intermittently monitor a patient for dysphagia and disable the swallow override routine when dysphagia is not detected.

19. The device of claim 16, wherein the event detector is configured to detect the dysphagia event during a programmed burst of neural stimulation pulses.

20. An implantable device, comprising:
- a neural stimulation circuit configured to deliver an autonomic modulation therapy (AMT) to treat a disease, including deliver neural stimulation according to a programmed schedule;
- an event detector configured to detect a laryngeal spasm,
- wherein the neural stimulation circuit includes a therapy override controller configured to respond to a detected laryngeal spasm, detected by the event detector, and override the programmed schedule for the AMT, wherein the therapy override controller is configured to respond to the detected laryngeal spasm by temporarily overriding the programmed schedule for a programmed time period, and
- wherein the neural stimulation circuit is configured to deliver intermittent neural stimulation with programmed bursts of neural stimulation pulses, wherein each programmed burst is a stimulation ON time separated from adjacent bursts in the programmed schedule by a stimulation OFF time.

21. The device of claim 20, wherein:
- the event detector is configured to monitor a patient for laryngeal spasms between bursts; and
- the therapy override controller is configured to deliver a subsequent burst if laryngeal spasm is not detected between bursts.

22. The device of claim 20, wherein:
- the event detector is configured to monitor a patient for laryngeal spasms during a burst to detect laryngeal spasms attributable to the neural stimulation; and
- the therapy override controller is configured to deliver a subsequent pulse in the burst if the spasm is not detected during the burst and temporarily override the programmed schedule if the spasm is detected during the burst.

* * * * *